(12) United States Patent
Williams et al.

(10) Patent No.: US 9,254,290 B2
(45) Date of Patent: Feb. 9, 2016

(54) METHOD FOR SCREENING DIABETES TREATING AGENT

(75) Inventors: Darren R. Williams, Gwangju (KR); Da-Woon Jung, Gwangju (KR); Young-Tae Chang, Busan (KR)

(73) Assignee: GWANGJU INSTITUTE OF SCIENCE AND TECHNOLOGY, Buk-Gu, Gwangju (KR)

( * ) Notice: Subject to any disclaimer, the term of this patent is extended or adjusted under 35 U.S.C. 154(b) by 127 days.

(21) Appl. No.: 13/702,170

(22) PCT Filed: Jul. 28, 2011

(86) PCT No.: PCT/KR2011/005553
§ 371 (c)(1),
(2), (4) Date: Jan. 9, 2013

(87) PCT Pub. No.: WO2012/015249
PCT Pub. Date: Feb. 2, 2012

(65) Prior Publication Data
US 2013/0115642 A1     May 9, 2013

(30) Foreign Application Priority Data
Jul. 29, 2010  (KR) .......................... 10-2010-0073670

(51) Int. Cl.
*A61K 31/53*     (2006.01)
*G01N 33/50*    (2006.01)
*C12Q 1/54*      (2006.01)

(52) U.S. Cl.
CPC ............ *A61K 31/53* (2013.01); *G01N 33/5008* (2013.01); *G01N 2800/042* (2013.01)

(58) Field of Classification Search
CPC ..... C12Q 1/54; A61K 31/53; G01N 33/5008; G01N 2800/042
See application file for complete search history.

(56) References Cited

U.S. PATENT DOCUMENTS

| 5,716,619 A | 2/1998 | Cooper et al. |
| 2007/0231812 A1 | 10/2007 | Itakura et al. |
| 2010/0285117 A1 | 11/2010 | Moinet et al. |
| 2011/0237587 A1 | 9/2011 | Cheon et al. |

FOREIGN PATENT DOCUMENTS

WO    WO 2004026844 A1  *  4/2004

* cited by examiner

*Primary Examiner* — Sarah Pihonak
*Assistant Examiner* — Jason A Deck
(74) *Attorney, Agent, or Firm* — Nath, Goldberg & Meyer; Joshua B. Goldberg; Christopher Thomas

(57) ABSTRACT

The present invention provides a method for screening a diabetes treating agent comprising the following steps: (a) preparing cells inside a culture medium; (b) treating the culture medium with a test substance; (c) treating the result of step (b) with a glucose derivative which is not metabolized; and (d) measuring the glucose derivative which has flowed into the cells, wherein the test substance is determined to be a diabetes treating agent if the test substance accelerates uptake of the glucose derivative in the cells. Therefore, the described pharmaceutical composition, including a triazin-based compound as an active ingredient, can be useful for application in preventing or treating diabetes.

3 Claims, 22 Drawing Sheets

Fig. 2a

Step 1: 104 cells of 3T3-L1 pre-adipocytes were seeded in a black, 96 well tissue culture plate; and the cells were cultured in DMEM supplemented 10% FBS and antibiotics.

↓ 48 hrs

Step 2: Adipocytes were induced to differentiate by treatments with 0.5 mM of 3-isobutyl-1-methyl-xanthine, 2 μg/ml of dexamethasone and 1 μg/ml of insulin.

↓ 48 hrs

Step 3: Cells were further cultured under 1 μg/ml of insulin.

↓ 7 days

Step 4: Cells were cultured in serum-free low glucose DMEM culture media (1 g/L glucose; 200 μL total volume/well).

↓ 1 hr

Step 5: Cells were treated with compounds of chemical library (10 μM).

↓ 1 hr

Step 6: Cells were cultured in serum-free low glucose DMEM culture media containing 20 μM of 6-NBDG.

↓ 30 min.

Step 7: Cells were washed three times with PBS and lysed with 70 μL of 0.1 M potassium phosphate buffer (pH 10) containing 1% triton x-100 treatment.

↓ Dark condition for 10 min.

Step 8: The lysate was added with 30 μL of DMSO and homogenized by pipetting.

↓ Immediately

Step 9: The fluorescent was measured using a fluorescent microplate reader ($\lambda_{ex}$ = 466 nm and $\lambda_{em}$ = 540 nm).

6-NBDG uptake: Insulin

6-NBDG uptake: compound AP-III-a4

6-NBDG uptake: compound AP-I-h7

6-NBDG uptake: NBDG only

Bar = 40 μm

METHOD FOR SCREENING DIABETES TREATING AGENT

This is a National Phase Application filed under 35 U.S.C. 371 as a national stage of PCT/KR2011/005553, filed Jul. 28, 2011, and claims priority benefit to Korean Application No. 10-2010-0073670, filed Jul. 29, 2010, the content of each of which is hereby incorporated by reference in its entirety.

FIELD OF THE INVENTION

The present invention relates to a method for screening a diabetes treating agent.

DESCRIPTION OF THE RELATED ART

Insulin is the only agent developed for the treatment of either type 1 diabetes or severe type 2 diabetes.[1,2] A number of synthetic small molecules, such as zinc (II) complexes and vanadium compounds, have been shown to mimic the action of insulin in cell culture and animal models of diabetes. In addition, many natural products, such as antibiotics (e.g. anisomycin), fungal metabolites (e.g. L-783,281), plant extracts (e.g. leaf alcoholic extract from the tropical herbaceous perennial *Catharanthus roseus*) and animal constituents (e.g. dried chrysalis of the silkworm *Bombyx Batryticatus*) also promote glucose uptake in cells.[3-6] However, none of these compounds or extracts have been able to replace insulin in the treatment of diabetes. Therefore, there is a need to search for new anti-diabetic agents that can mimic the effect of insulin. In addition, the characterization of new insulin mimetic agents can promote the discovery of new drug targets that further our understanding of the biochemical mechanisms producing diabetes and insulin resistance.

Measurements of glucose uptake in cells have usually employed radioactive glucose isotopes. The high signal to noise ratio of these isotopes is favorable for kinetic studies of glucose transport. However, the inconvenience and expense associated with radioactive waste disposal and cleanup tends to preclude their use for large-scale screening programs to discover new modulators of glucose uptake.

Two fluorescent tagged glucose analogues are available for studying glucose homeostasis. 6-(N-(7-nitrobenz-2-oxa-1,3-diazol-4-yl)amino)-6-deoxyglucose (6-NBDG) was developed in 1985 for studying glucose transporter 1 (GLUT 1).[7] 2-NBDG was developed in 1996 for studying glucose uptake in bacteria.[8] The fate of 2- and 6-NBDG differ upon cellular uptake. 2-NBDG enters the glycolytic pathway; being phosphorylated by hexokinase and rapidly degraded to non-fluorescent products.[8] In contrast, 6-NBDG cannot be phosphorylated by hexokinase and accumulates in the cytoplasm in its fluorescent form.

There have been concerns about the specificity of NBDG probes and there is relatively little knowledge about how glucose transporters interact with NBDG. For example, glucose is a poor competitor of 6-NBDG uptake, raising the prospect that alternative cellular pathways mediate NBDG uptake.[9] However, recent research has shown that 6-NBDG binds to GLUT 1 with 300 times greater affinity than glucose, suggesting that kinetic inconsistencies associated with the use of NBDG are only ostensible.[9]

Two approaches have previously been used to establish a protocol based on NBDG that would allow the screening and identification of new regulators of glucose uptake. The first approach, based on flow cytometry, has produced mixed results. One research group reported that insulin-stimulated 6-NBDG uptake could be detected in human monocyte cells.[10] In contrast, a second research group failed to detect insulin-stimulated 2-NBDG uptake in either hepatocyte or skeletal muscle cell lines.[11] A second approach, based on fluorescence-based microplate reader analysis, detected cytotoxicity-associated 2-NBDG uptake in human lung fibroblasts induced by the diarrhetic shellfish poison, okadaic acid.[12] However, to date, there has been no published data about the use of NBDG to establish a screening system that can successfully detect new compounds that regulate glucose uptake.

Throughout this application, several patents and publications are referenced and citations are provided in parentheses. The disclosure of these patents and publications is incorporated into this application in order to more fully describe this invention and the state of the art to which this invention pertains.

DETAILED DESCRIPTION OF THIS INVENTION

Technical Purposes of this Invention

The present inventors have made intensive studies to develop a novel drug for mimicking the activity of insulin (insulin mimetics). As a result, the present inventors have constructed a novel NBDG screening system which can screen compounds promoting glucose uptake in adipocytes with a high-throughput screening method, and they have found that triazin-based compounds for effective in diabetes were screened using the screening system of the present invention from a chemical library of 576 tagged traizine-based small molecules and verified experimentally insulin mimetics thereof.

Accordingly, it is an object of this invention to provide a method for screening a diabetes treating agent.

Other objects and advantages of the present invention will become apparent from the detailed description to follow taken in conjugation with the appended claims and drawings.

Technical Solutions of this Invention

In one aspect of the present invention, there is provided a method for screening an agent for treatment of diabetes, comprising: (a) preparing cells in a culture medium; (b) contacting a test substance to the culture medium; (c) contacting the resultant of the step (b) to a non-metabolizable glucose analogue; and (d) measuring the glucose analogue uptaken into the cells, wherein where the test substance is measured to promote uptake of the glucose analogue in the cells, the test substance is determined to be the agent for treatment of diabetes.

The present inventors have made intensive studies to develop a novel drug for mimicking the activity of insulin (insulin mimetics). As a result, the present inventors have constructed a novel NBDG screening system which can screen compounds promoting glucose uptake in adipocytes with a high-throughput screening method, and they have found that triazin-based compounds for effective in diabetes were screened using the screening system of the present invention from a chemical library of 576 tagged traizine-based small molecules and verified experimentally insulin mimetics thereof.

The present invention provides a method for screening a compound for preventing or treating diabetes with measuring cellular glucose uptake using glucose analogue, more preferably non-metabolizable glucose analogue.

According to the present method, cells are first prepared in a culture medium. Cells used in the present invention include, but not limited to, more preferably hepatocytes, skeletal muscle cells or adipocytes, still more preferably hepatocytes, myoblasts or pre-adipocytes and most preferably adipocytes. Pre-adipocytes used in the present invention are 3T3-L1 murine embryonic fibroblasts.

According to a preferred embodiment, the cells are insulin-resistant by treatment with insulin.

According to a preferred embodiment, the method of the present invention may further comprise the step (pre-a) of differentiating cells to adipocytes before the step (a). The cells as mentioned above are induced to differentiate into adipocytes by treatment with insulin. Then, the cells are further cultured under treatment with insulin. In the present invention, 3T3-L1 adipocytes are used for experiments 8 days after the induction of differentiation.

Afterwards, the cultured cells are contacted with a test substance. The term "test substance" used herein in conjunction with the present screening method refers to a material tested in the present method for analyzing the influence on the glucose uptake of cells used in the present invention. The test substance includes a chemical library, a natural product library, nucleotides, antisense-RNA and siRNA (small interference RNA), but not limited to. More preferably, the test substance of the present invention includes a chemical library and most preferably a chemical library of tagged traizine-based small molecules.

According to a preferred embodiment, the test substance used in the present invention is a chemical library of 576 tagged traizine-based small molecules.

After treatment of the test substance, the resultant is contacted with a glucose analogue in the culture medium and the cells are cultured. More preferably, the glucose analogue is a non-metabolizable glucose analogue and most preferably 6-(N-(7-nitrobenz-2-oxa-1,3-diazol-4-yl)amino)-6-deoxy-glucose (6-NBDG). 6-NBDG is a fluorescent glucose analogue available for monitoring glucose uptake and movement in live cell and cannot be hydrolyzed in cells. It has the molecular formula of $C_{12}H_{14}N_4O_8$ and the structure represented by the following chemical formula:

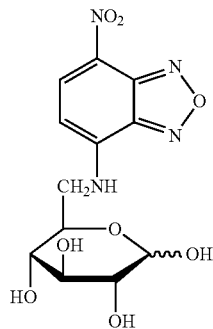

Although 6-NBDG is sensitive to the environment, it appear its typical excitation/emission spectra at approximately 465/540 nm. Therefore, it can be visualized under a microscope using appropriate optical filters.

Finally, the glucose analogue is detected in the cells as mentioned above. According to a preferred embodiment, the detection of the glucose analogue may be easily and simply carried out by fluorescence measurement. At this time, where the test substance is measured to promote uptake of the glucose analogue in the cells, the test substance is determined to be the agent for treatment of diabetes.

The term used herein "promotion" refers to an increase of the fluorescence detection signal detected in cell lysates, more preferably an increase of the fluorescence signal emitted from the glucose analogue which is uptaken into cells by the treatment of the test substance.

According to a preferred embodiment, the agent for treatment of diabetes to be screened includes an agent for treatment of type 2 diabetes caused by insulin resistance, but not limited to.

According to a preferred embodiment, the triazine-based compound used in the present invention comprises compounds represented by the following Formula I:

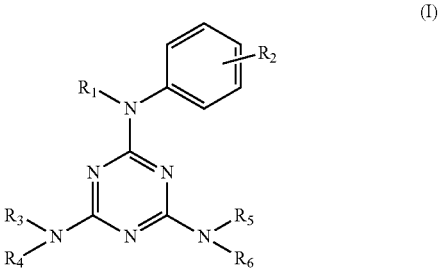

wherein, $R_1$ is H, or straight or branched $C_1$-$C_5$ alkyl; $R_2$ is H, straight or branched $C_1$-$C_5$ alkyl, straight or branched $C_1$-$C_5$ alkyl alcohol, —[(CH$_2$)$_m$—O]$_n$—(CH$_2$)$_p$—NH$_2$ (each of m, n and p is an integer of 1 to 10, respectively), —[(CH$_2$)$_m$—O]$_n$—CH$_3$ (each of m and n is an integer of 1 to 10, respectively), —[(CH$_2$)$_m$—O]$_n$—(CH$_2$)$_p$—CH$_3$ (each of m, n and p is an integer of 1 to 10, respectively), —(CH$_2$)$_q$—(CONH)—C$_{1-5}$ straight or branched alkyl (q is an integer of 0 to 5), —(CH$_2$)$_q$—(CONH)—C$_{1-5}$ straight or branched alkyl alcohol (q is an integer of 0 to 5), —(CH$_2$)$_q$—(CONH)—[(CH$_2$)$_m$—O]$_n$—(CH$_2$)$_p$—NH$_2$ (each of m, n and p is an integer of 1 to 10, respectively, and q is an integer of 0 to 5), —(CH$_2$)$_q$—(CONH)—[(CH$_2$)$_m$—O]$_n$—CH$_3$ (each of m and n is an integer of 1 to 10, respectively, and q is an integer of 0 to 5) or —(CH$_2$)$_q$—(CONH)—[(CH$_2$)$_m$—O]$_n$—(CH$_2$)$_p$—CH$_3$ (each of m, n and p is an integer of 1 to 10, respectively, and q is an integer of 0 to 5); each of $R_3$, $R_4$, $R_5$ and $R_6$ is independently H, straight or branched $C_1$-$C_{10}$ alkyl, straight or branched $C_1$-$C_{10}$ alkyl alcohol, $C_6$-$C_{10}$ aryl, $C_7$-$C_{16}$ aralkyl, $C_7$-$C_{16}$ alkaryl, $C_3$-$C_{15}$ cycloalkyl, $C_4$-$C_{20}$ alkyl cycloalkyl; aryl group of the aralkyl may be substituted with $C_1$-$C_5$ alkyl, $C_1$-$C_5$ alkoxy or halogen; a ring carbon of the alkyl cycloalkyl may be substituted with straight or branched $C_1$-$C_5$ alkyl; and $R_3$ and $R_4$ or $R_5$ and $R_6$ may be linked to each other to form $C_3$-$C_{10}$ cyclic alkyl in which $C_3$-$C_{10}$ cyclic alkyl may comprise oxygen or nitrogen as a heteroatom; and the heteroatom may be substituted with $C_6$-$C_{10}$ aryl or $C_6$-$C_{10}$ aryl having halogen or nitro substituent.

The triazine-based compound as an active ingredient of the present invention is identified as insulin mimetics using the screening system of the present invention from a chemical library of 576 tagged traizine-based small molecules which is constructed by the inventors. The details of synthesis methods and its uses for the chemical library of triazine-based compound used in the present invention can be found in international publication number WO 03/032903 and WO 03/050237, the teachings of which are incorporated herein by reference in its entity.

The term "$C_1$-$C_{10}$ alkylamine" in the Formula I of the present invention refers to an amine having an alkyl group of a straight chain or a branched chain containing methylamine, ethylamine, n-propylamine, isopropylamine, n-butylamine, sec-butylamine, tert-butylamine, n-amyl and tert-amyl.

The term used herein "$C_1$-$C_{10}$ alkyl of a straight chain or a branched chain" in the present invention refers to an alkyl group of a straight chain or a branched chain containing methylamine, ethylamine, n-propylamine, isopropylamine, n-butylamine, sec-butylamine, tert-butylamine, n-amyl, tert-amyl or hexyl. The term "alkyl alcohol" in the Formula I of the present invention includes methanol, ethanol, propanol, butanol, benzyl alcohol, phenethyl alcohol and its analogues, but not limited to.

The term used herein "aryl" refers to a substituted or unsubstituted, monocyclic or polycyclic carbon ring which is entirely or partially unsaturated. Preferably, the aryl may be monoaryl or biaryl. Aryl group includes phenyl group, substituted phenyl group, naphthyl group and substituted naphthyl group, but not limited to. Preferably, the aryl group substituent as mentioned above includes a small number of alkyl or halogen.

The term used herein "aryl group substituent" includes alkyl, cycloalkyl, aryl, cycloaryl and heteroaryl. Alternatively, it includes at least one substituent selected from the group consisting of halo, haloalkyl, alkyl, arylalkyl, heteroarylalkyl, alkenyl having 1-2 double bond, alkynyl having 1-2 triple bond, hydroxy and polyhaloalkyl, preferably 1-3 substituent. More preferably, aryl group substituent includes $C_1$-$C_5$ alkyl, $C_1$-$C_5$ alkoxy or halogen.

The term used herein "$C_1$-$C_5$ alkoxy" for example, includes methoxy, ethoxy or propoxy, but not limited to.

The term used herein "$C_7$-$C_{16}$ aralkyl" refers to a $C_1$-$C_{10}$ alkyl substituted with one, or two or more phenyl rings in a random position, and for example, includes benzyl, 2-phenylethyl, 3-phenyl(n-prop-1-yl), 4-phenyl (hex-1-yl), 3-phenyl(n-am-2-yl) or 3,3-diphenylpropyl, but not limited to.

The term used herein "$C_3$-$C_{15}$ cycloalkyl" refers to a saturated hydrocarbon with a mono- or multi-ring structure consisting of 3 to 15 carbon atoms, more preferably 3 to 10 carbon atoms. For example, $C_3$-$C_{15}$ cycloalkyl includes, but not limited to, cyclopropyl ring, cyclobutyl ring, cyclohexyl ring or cycloheptyl ring.

The term used herein "$C_4$-$C_{20}$ alkylcycloalkyl" refers to an alkyl consisting of 4 to carbon atoms, which is substituted with an alkyl in the above-described cycloalkyl.

The term used herein "halogen" includes F, Cl, Br and I.

According to a preferred embodiment, in the Formula I of the present invention $R_1$ includes H or $C_1$-$C_2$ alkyl and more preferably H.

According to a preferred embodiment, in the Formula I of the present invention $R_2$ includes H, straight or branched $C_1$-$C_5$ alkyl, straight or branched $C_1$-$C_5$ alkyl alcohol, —[(CH$_2$)$_m$—O]$_n$—(CH$_2$)$_p$—NH$_2$ (each of m, n and p is an integer of 1 to 10, respectively), —[(CH$_2$)$_m$—O]$_n$—CH$_3$ (each of m and n is an integer of 1 to 10, respectively), —[(CH$_2$)$_m$—O]$_n$—(CH$_2$)$_p$—CH$_3$ (each of m, n and p is an integer of 1 to 10, respectively), —(CH$_2$)$_q$—(CONH)—C$_{1-5}$ straight or branched alkyl (q is an integer of 0 to 5), —(CH$_2$)$_q$—(CONH)—C$_{1-5}$ straight or branched alkyl alcohol (q is an integer of 0 to 5), —(CH$_2$)$_q$—(CONH)—[(CH$_2$)$_m$—O]$_n$—(CH$_2$), —NH$_2$ (each of m, n and p is an integer of 1 to 10, respectively, and q is an integer of 0 to 5), —(CH$_2$)$_q$—(CONH)—[(CH$_2$)$_m$—O]$_n$—CH$_3$ (each of m and n is an integer of 1 to 10, respectively, and q is an integer of 0 to 5) or —(CH$_2$)$_q$—(CONH)—[(CH$_2$)$_m$—O]$_n$—(CH$_2$)$_p$—CH$_3$ (each of m, n and p is an integer of 1 to 10, respectively, and q is an integer of 0 to 5), and more preferably H, straight or branched $C_1$-$C_5$ alkyl, straight or branched $C_1$-$C_5$ alkyl alcohol, —[(CH$_2$)$_m$—O]$_n$—(CH$_2$)$_p$—NH$_2$ (each of m, n and p is an integer of 1 to 5, respectively), —[(CH$_2$)$_m$—O]$_n$—CH$_3$ (each of m and n is an integer of 1 to 5, respectively), —[(CH$_2$)$_m$—O]$_n$—(CH$_2$)$_p$—CH$_3$ (each of m, n and p is an integer of 1 to 5, respectively), —(CH$_2$)$_q$—(CONH)—C$_{1-5}$ straight or branched alkyl (q is an integer of 0 to 2), —(CH$_2$)$_q$—(CONH)—C$_{1-5}$ is straight or branched alkyl alcohol (q is an integer of 0 to 2), —(CH$_2$)$_q$—(CONH)—[(CH$_2$)$_m$—O]$_n$—(CH$_2$)$_p$—NH$_2$ (each of m, n and p is an integer of 1 to 5, respectively, and q is an integer of 0 to 2), —(CH$_2$)$_q$—(CONH)—[(CH$_2$)$_m$—O]$_n$—CH$_3$ (each of m and n is an integer of 1 to 5, respectively, and q is an integer of 0 to 2) or —(CH$_2$)$_q$—(CONH)—[(CH$_2$)$_m$—O]$_n$—(CH$_2$)$_p$—CH$_3$ (each of m, n and p is an integer of 1 to 5, respectively, and q is an integer of 0 to 2).

According to a preferred embodiment, in the Formula I of the present invention $R_3$ and $R_4$ include independently H, straight or branched $C_1$-$C_{10}$ alkyl, straight or branched $C_1$-$C_{10}$ alkyl alcohol, $C_6$-$C_{10}$ aryl, $C_7$-$C_{16}$ aralkyl, $C_7$-$C_{16}$ alkaryl, $C_3$-$C_{15}$ cycloalkyl, $C_4$-$C_{20}$ alkyl cycloalkyl; aryl group of the aralkyl may be substituted with $C_1$-$C_5$ alkyl, $C_1$-$C_5$ alkoxy or halogen; a ring carbon of the alkyl cycloalkyl may be substituted with straight or branched $C_1$-$C_5$ alkyl; and $R_3$ and $R_4$ or $R_5$ and $R_6$ may be linked to each other to form $C_3$-$C_{10}$ cyclic alkyl in which $C_3$-$C_{10}$ cyclic alkyl may comprise oxygen or nitrogen as a heteroatom; and the heteroatom may be substituted with $C_6$-$C_{10}$ aryl or $C_6$-$C_{10}$ aryl having halogen or nitro substituent, and more preferably independently H, straight or branched $C_1$-$C_5$ alkyl, straight or branched $C_1$-$C_5$ alkyl alcohol, $C_6$-$C_{10}$ aryl, $C_7$-$C_{16}$ aralkyl, $C_7$-$C_{16}$ alkaryl, $C_5$-$C_6$ cycloalkyl, $C_7$-$C_{10}$ alkyl cycloalkyl; aryl group of the aralkyl may be substituted with $C_1$-$C_3$ alkyl or halogen; a ring carbon of the alkyl cycloalkyl may be substituted with straight or branched $C_1$-$C_5$ alkyl; and $R_3$ and $R_4$ or $R_5$ and $R_6$ may be linked to each other to form $C_4$-$C_6$ cyclic alkyl in which $C_4$-$C_6$ cyclic alkyl may comprise oxygen or nitrogen as a heteroatom; and the heteroatom may be substituted with $C_6$-$C_{10}$ aryl or $C_6$-$C_{10}$ aryl having halogen or nitro substituent.

According to a preferred embodiment, the triazine-based compound represented by the following Formula I which is identified by the method of the present invention includes compounds represented by the following Formulae 1-12:

[Formula 1]

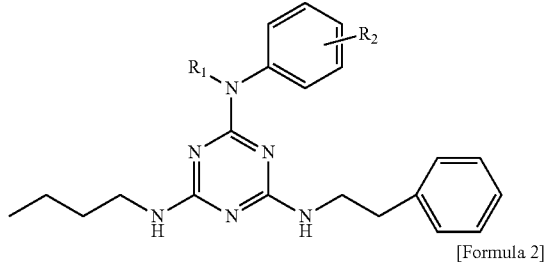

[Formula 2]

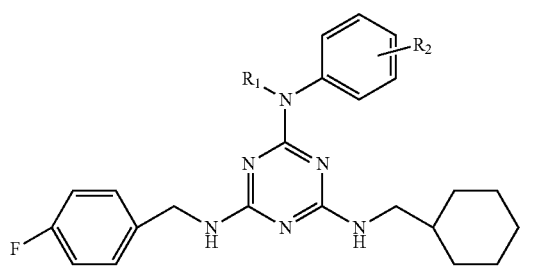

[Formula 3]
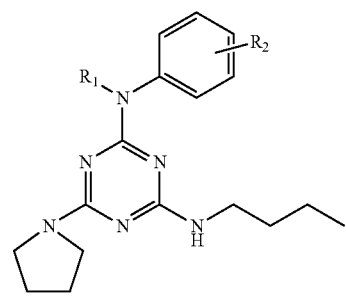
[Formula 4]
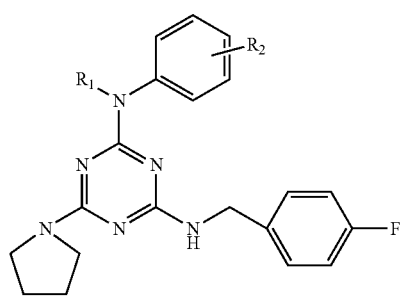
[Formula 5]
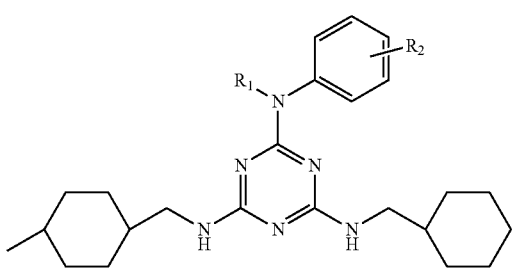
[Formula 6]
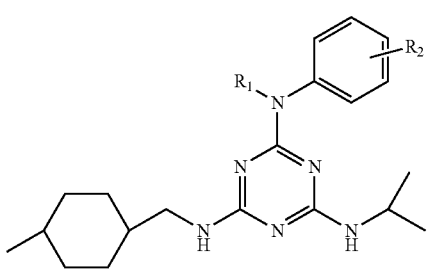
[Formula 7]
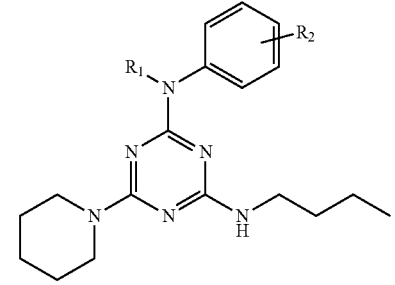
[Formula 8]
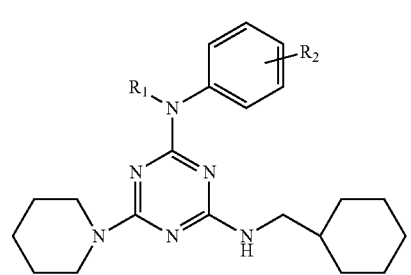
[Formula 9]
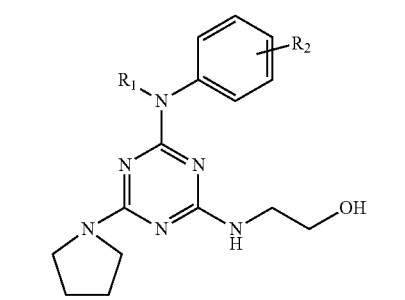
[Formula 10]
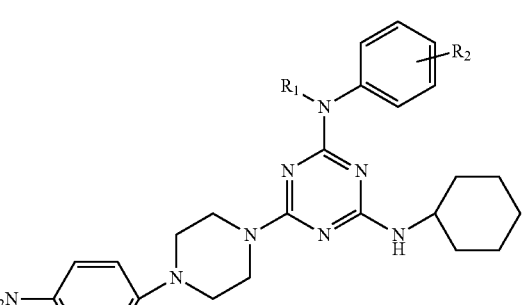
[Formula 11]
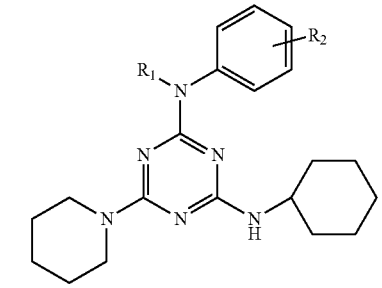
[Formula 12]
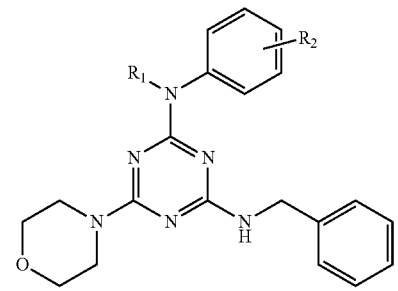
wherein, $R_1$ is H, or straight or branched $C_1$-$C_5$ alkyl; $R_2$ is H, straight or branched $C_1$-$C_5$ alkyl, straight or branched $C_1$-$C_5$ alkyl alcohol, —[(CH$_2$)$_m$—O]$_n$—(CH$_2$)$_p$—NH$_2$ (each of m, n and p is an integer of 1 to 10, respectively), —[(CH$_2$)$_m$—O]$_n$—CH$_3$ (each of m and n is an integer of 1 to 10, respectively), —[(CH$_2$)$_m$—O]$_n$—(CH$_2$)$_p$—CH$_3$ (each of m, n and p is an integer of 1 to 10, respectively), —(CH$_2$)$_q$—(CONH)—C$_{1-5}$ straight or branched alkyl (q is an integer of 0 to 5), —(CH$_2$)$_q$—(CONH)—C$_{1-5}$ straight or branched alkyl alcohol (q is an integer of 0 to 5), —(CH$_2$)$_q$—(CONH)—[(CH$_2$)$_m$—O]$_n$—(CH$_2$)$_p$—NH$_2$ (each of m, n and p is an integer of 1 to 10, respectively, and q is an integer of 0 to 5), —(CH$_2$)$_q$—(CONH)—[(CH$_2$)$_m$—O]$_n$—CH$_3$ (each of m and n is an integer of 1 to 10, respectively, and q is an integer of 0 to 5) or —(CH$_2$)$_q$—(CONH)—[(CH$_2$)$_m$—O]$_n$—(CH$_2$)$_p$—CH$_3$ (each of m, n and p is an integer of 1 to 10, respectively, and q is an integer of 0 to 5).

More preferably, the triazine-based compound represented by the following Formulae 1-12 which is identified by the method of the present invention includes compounds represented by the following Formulae 13-24:

[Formula 13]

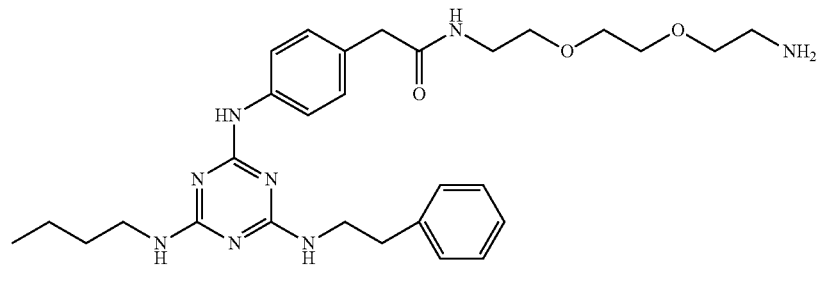

AP-I-h7

[Formula 14]

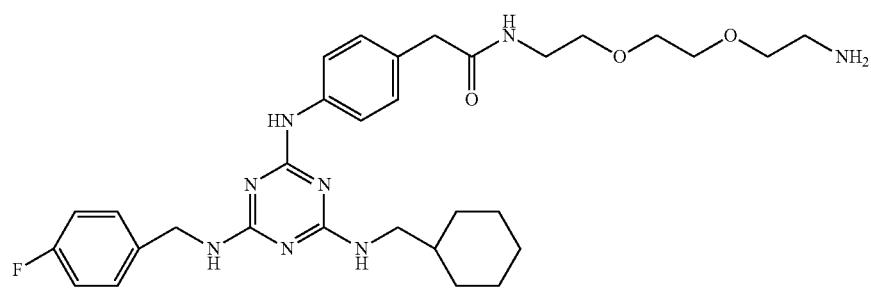

AP-III-a4

[Formula 15]

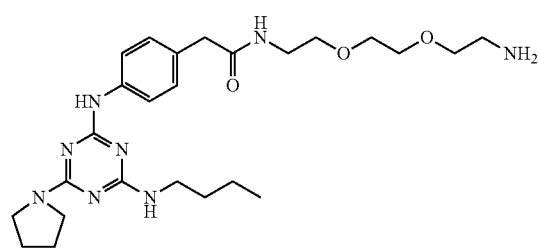

AP-IV-g3

[Formula 16]

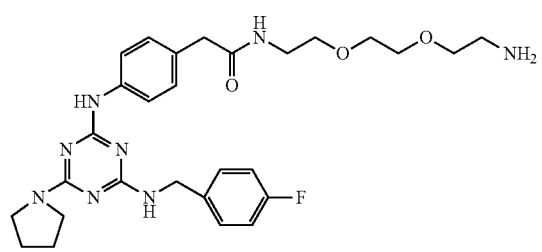

AP-IV-g8

[Formula 17]

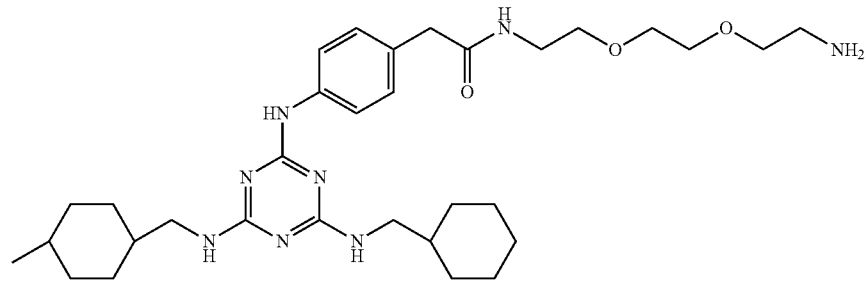

AP-IV-a4

[Formula 18]
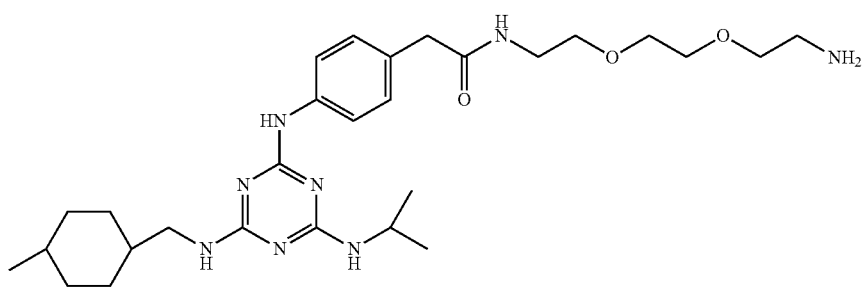
AP-IV-a10
[Formula 19]
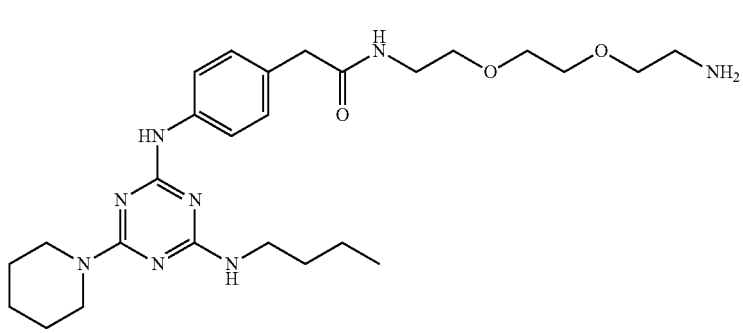
AP-IV-e3
[Formula 20]
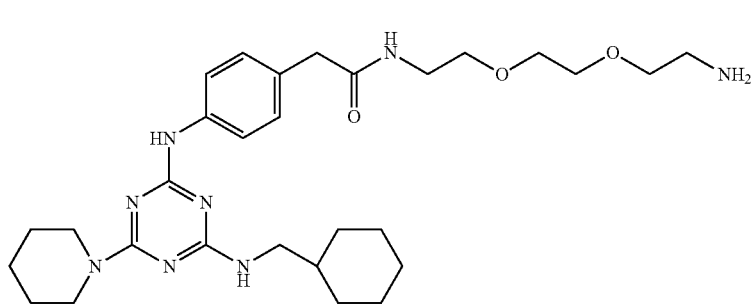
AP-IV-e4
[Formula 21]
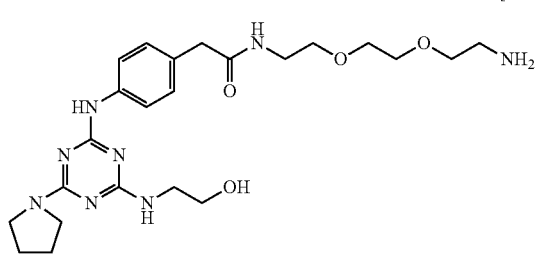
AP-IV-g12
[Formula 22]
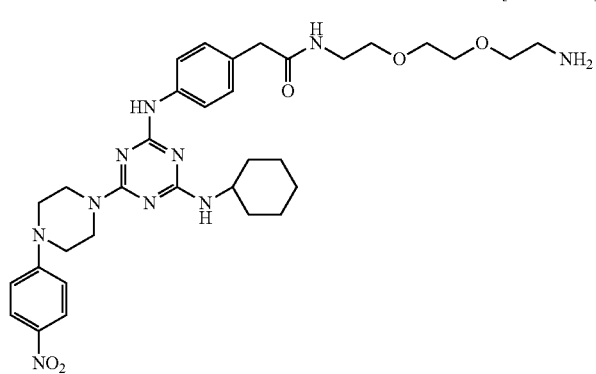
AP-IV-b5

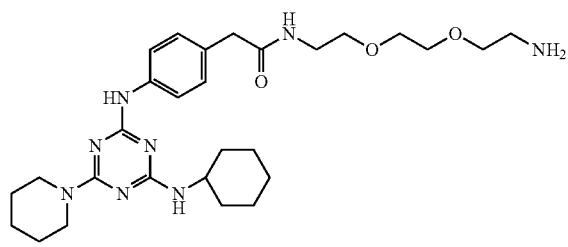

AP-IV-e5

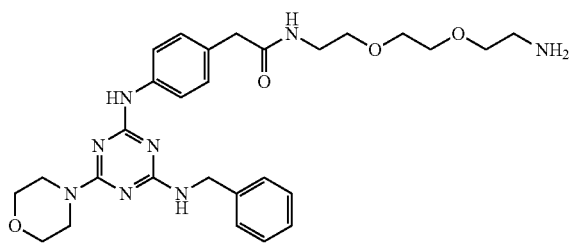

AP-IV-h2

Most preferably, the triazine-based compound represented by the following Formulae 1-12 which is identified by the method of the present invention includes: compounds represented by the following Formulae 13 or 14:

[Formula 13]

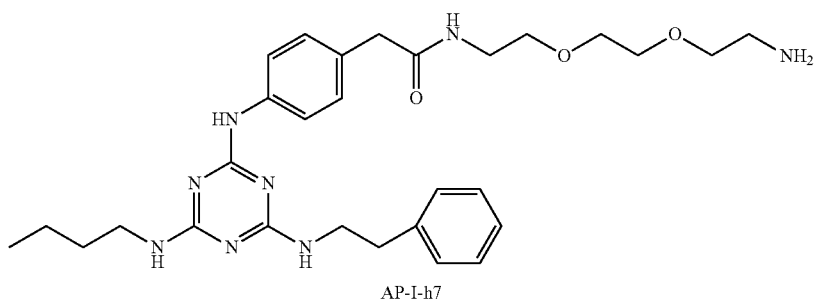

AP-I-h7

[Formula 14]

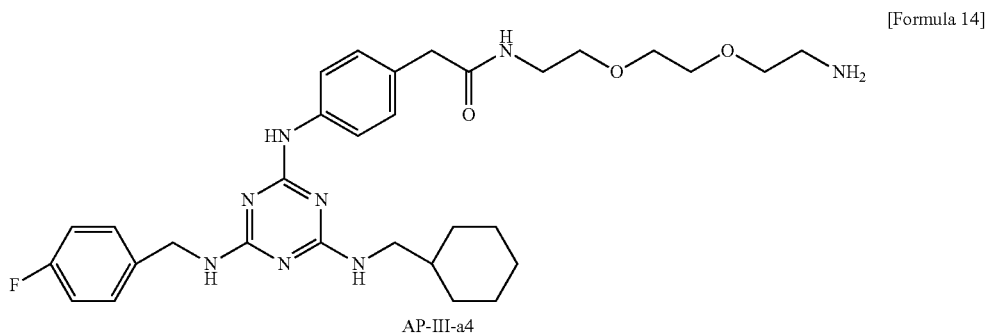

AP-III-a4

According to a preferred embodiment, the triazine-based compound represented by the following Formula I which is identified by the method of the present invention promotes insulin mimetics, i.e., glucose uptake in the cells.

According to a preferred embodiment, the triazine-based compound represented by the following Formula I does not induce apoptosis to cause cytotoxicity in cells such that it has an anti-inflammatory activity.

Effects of this Invention

The features and advantages of the present invention will be summarized as follows:

(a) The present invention provides a method for screening a novel triazine-based compound having insulin mimetics.

(b) The triazine-based compound identified by the method of the present invention presents activity which promotes glucose uptake in the cells.

(c) In addition, the triazine-based compound of the present invention does not cause cytotoxicity such that it has an anti-inflammatory activity.

(d) Therefore, the described pharmaceutical composition comprising a triazin-based compound as an active ingredient may be useful in application for preventing or treating a diabetes.

EXAMPLES OF THE INVENTION

Figure 1A:
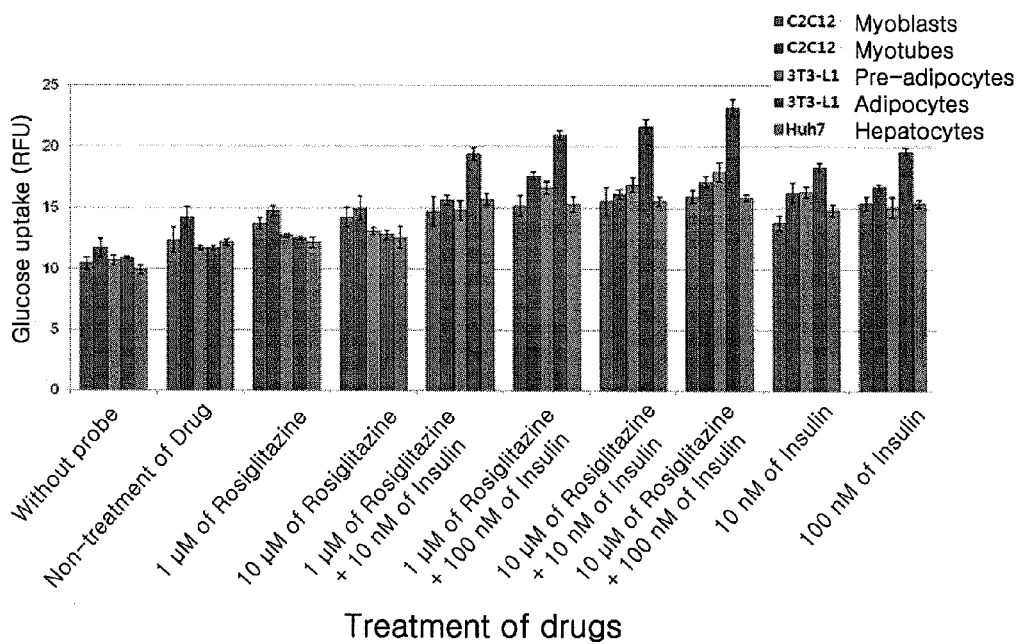
FIG. 1a represents results of 2-NBDG uptake in cell lines derived from the major insulin responsive body tissues. Differentiated 3T3-L1 adipocytes showed the greatest responsiveness to insulin and/or rosiglitazone-stimulated 2-NBDG uptake, compared to Huh7 hepatocytes, C2C12 myoblasts, C2C12 myotubes and 3T3-L1 pre-adipocytes. Cells were seeded at $10^4$ cells/well in black 96-well culture plates. 24 hrs later cells were treated with rosiglitazone for 24 hrs. Cells were incubated for 3 hrs in serum-free culture media before treatment with insulin for 30 min. *=P<0.05 compared to 3T3-L1 pre-adipocytes. Error=SD; 5 wells of a 96-well plate/ data point.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods

Reagents and Antibodies 2-(N-(7-nitrobenz-2-oxa-1,3-diazol-4-yl)amino)-2-deoxyglucose (2-NBDG) and the nonmetabolizable 6-(N-(7-nitrobenz-2-oxa-1,3-diazol-4-yl)amino)-6-deoxyglucose (6-NBDG) were purchased from Invitrogen (OR USA). Insulin from bovine pancreas, zinc sulfate, 4,6-ethylidine-D-glucose (4,6-EDG), cytochalasin B, epinephrine and staurosporine were purchased from Sigma-Aldrich (SL, USA). Rosiglitazine was purchased from Cayman Chemicals (MI, USA). Human tumor necrosis factor-alpha (TNF-α) was a gift from Professor Joo Young Lee, School of Life Sciences, Gwangju Institute of Science and Technology. An antibody against glyceraldehyde 3 phosphate dehydrogenase (GAPDH; antibody code 6C5) was purchased from Abcam (MA, USA). An antibody against vascular cell adhesion molecule-1 (VCAM-1; antibody code sc-13160) was a gift from professor Chang-Duk Jun, School of Life Sciences, Gwangju Institute of Science and Technology.

Cell Culture

C2C12 murine skeletal muscle precursor cells (myoblasts), 3T3-L1 murine embryonic fibroblasts and Huh7 human hepatocellular carcinoma were a gift from Professor Hyun Chul Lee, Yonsei University College of Medicine, Seoul. Myoblasts were maintained in proliferation media, consisting of Dulbecco's Modified Eagle's Medium (DMEM) supplemented with 10% fetal bovine serum (FBS), 50 units/mL penicillin and 50 µg/mL streptomycin. Myoblasts were induced to differentiate into skeletal muscle myotubes by culture for 8 days in differentiation media, consisting of Dulbecco's Modified Eagle's Medium (DMEM) supplemented with 5% horse serum, 50 units/mL penicillin and 50 µg/mL streptomycin. Differentiation media was replenished every 48 h.

3T3-L1 murine fibroblasts were maintained in proliferation media, consisting of DMEM supplemented with 10% FBS, 50 units/mL penicillin and 50 µg/mL streptomycin. 3T3-L1 fibroblasts were induced to differentiate into adipocytes as follows: 48 h postconfluent cells (designated day 0) were cultured in DMEM supplemented 10% FBS, 0.5 mM 3-isobutyl-1-methyl-xanthine, 2 µg/ml dexamethasone, 1 µg/ml insulin, 50 units/mL penicillin and 50 µg/mL streptomycin for 2 days. Every 2 days thereafter, the cells were incubated with fresh DMEM supplemented with 10% FBS and 1 µg/ml insulin. 3T3-L1 adipocytes were used for experiments 8 days after the induction of differentiation.

Huh7 human heptocytes were maintained in proliferation media, consisting of DMEM supplemented with 10% FBS, 50 units/mL penicillin and 50 µg/mL streptomycin.

THP-1 human monocytes were maintained in proliferation media, consisting of RPMI-1640 medium supplemented with 0.05 nM 2-mercaptoethanol, 10% FBS, 50 units/mL penicillin and 50 µg/mL streptomycin.

Human aortic endothelial cells were supplied by Cambrex (NJ, USA) and cultured in EBM-2 growth media supplemented with the EGM-2 bullet kit. THP-1 human monocytic cells were cultured in RPMI-1640 medium supplemented with 0.05 nM 2-mercaptoethanol, 10% fetal bovine serum and antibiotics. Cells were cultured in growth media containing 5 mM glucose for the normoglycemia condition or 30 mM glucose for the hyperglycemia condition.

Establishment of Cell-Based Screening System Based on NBDG Uptake

Three cell lines were chosen to test if NBDG can be used to detect insulin-stimulated glucose uptake in a 96 well plate culture format, which is more suitable for cell-based screening to identify novel insulin mimetic compounds. The cell lines chosen were Huh7 hepatocytes, C2C12 myoblasts and 3T3-L1 pre-adipocytes, which represent the major body tissue types that are sensitive to the action of insulin (liver, muscle and fat). $10^4$ cells/well were seeded in a black, 96 well tissue culture plate (BD Falcon, NJ, USA). C2C12 myoblasts and 3T3-L1 adipocytes were induced to undergo differentiation into myotubes and adipocytes, respectively, to compare the NDBG signal in proliferating and differentiated cells. NBDG uptake was measured following treatment with 10 nM or 100 nM insulin, and 1 µM or 10 µM rosiglitazone (an insulin-sensitizing agent), using a fluorescent microplate reader (SpectraMAX GeminiXS and SoftMax Pro V5 software, Molecular Devices, CA, USA). Cells were cultured in serum-free low glucose culture media for 3 h before the addition of insulin.

Figure 2B:
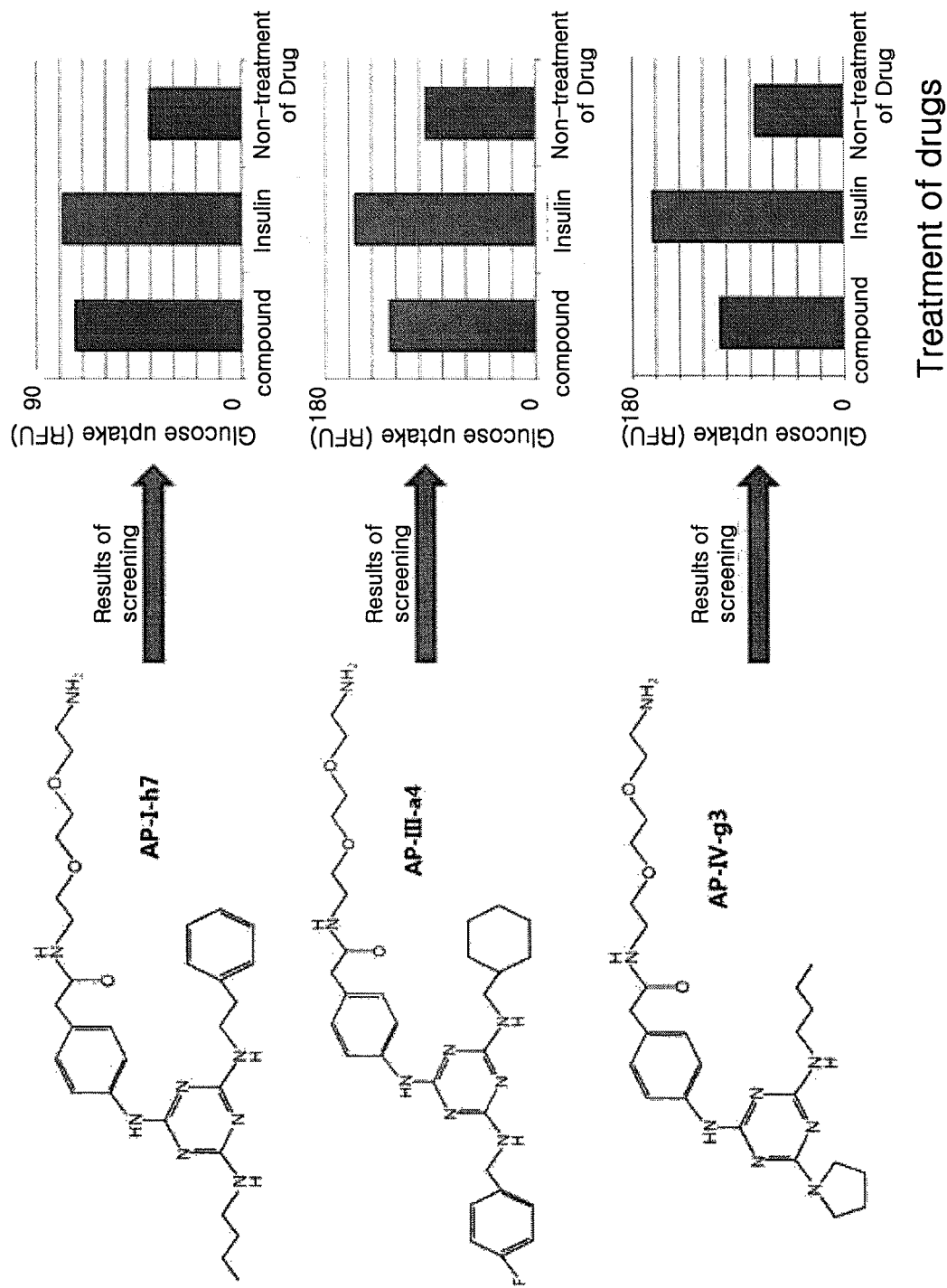
FIG. 2b represents chemical structures of novel compounds that modulate glucose uptake, identified from screening a triazine-based chemical library of 576 compounds. R1 and R2 functional groups are shown in pink and green, respectively (to denote inhibitors of NBDG uptake) or red (to denote inhibitors of NBDG uptake).
Figure 2C:
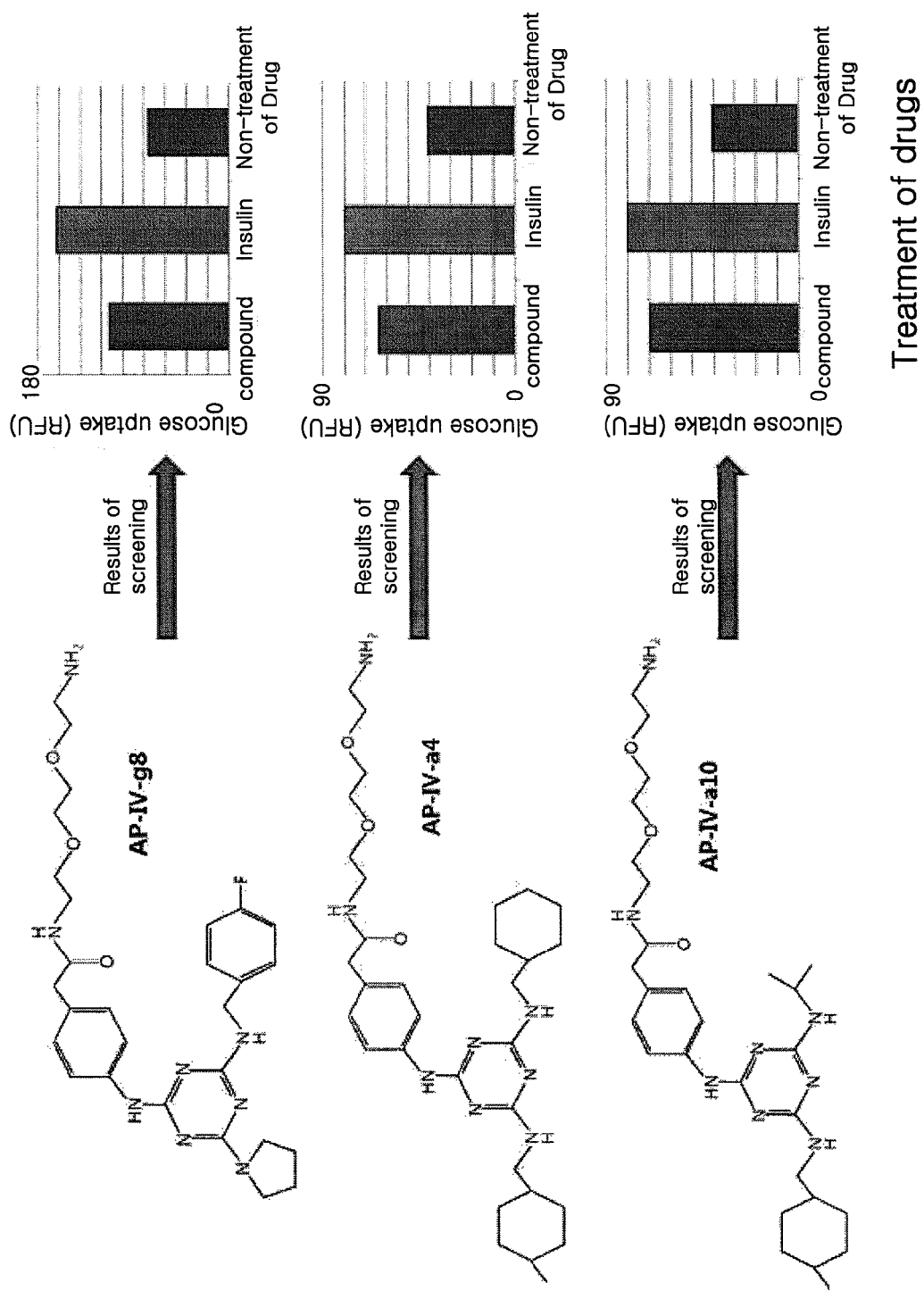
FIGS. 2c-2f represent re-testing of purified stocks of triazine-based compounds AP-III-a4, AP-IV-e3, AP-IV-e4 and AP-I-h7 confirmed that they promote NBDG uptake in adipocytes. Compounds were tested at a number of concentrations ranging from 250 nM-20 µM and compared with insulin and the known insulin mimetic compound, zinc sulfate. Error=SD. 3 wells of a 96-well plate/data point. *=P<0.05 compared to no treatment. Data in FIGS. 2c-2f is representative of three independent experiments.
Figure 2D:
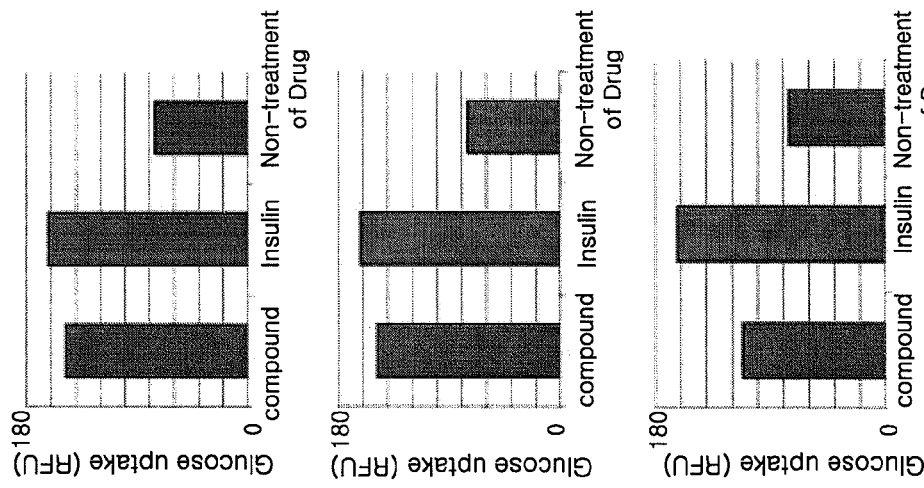
Figure 2D:
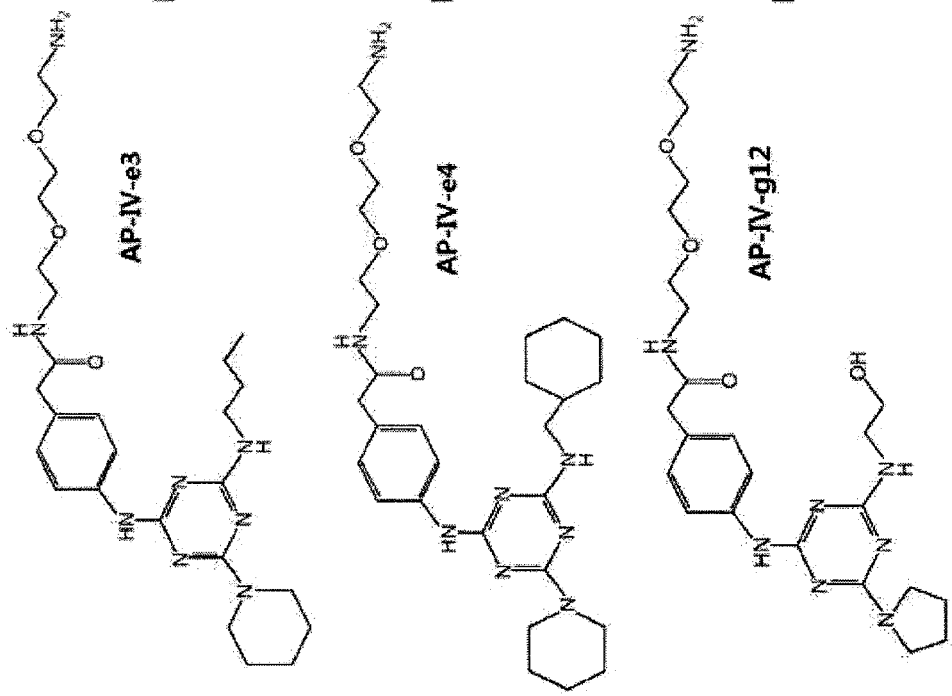
Figure 2E:
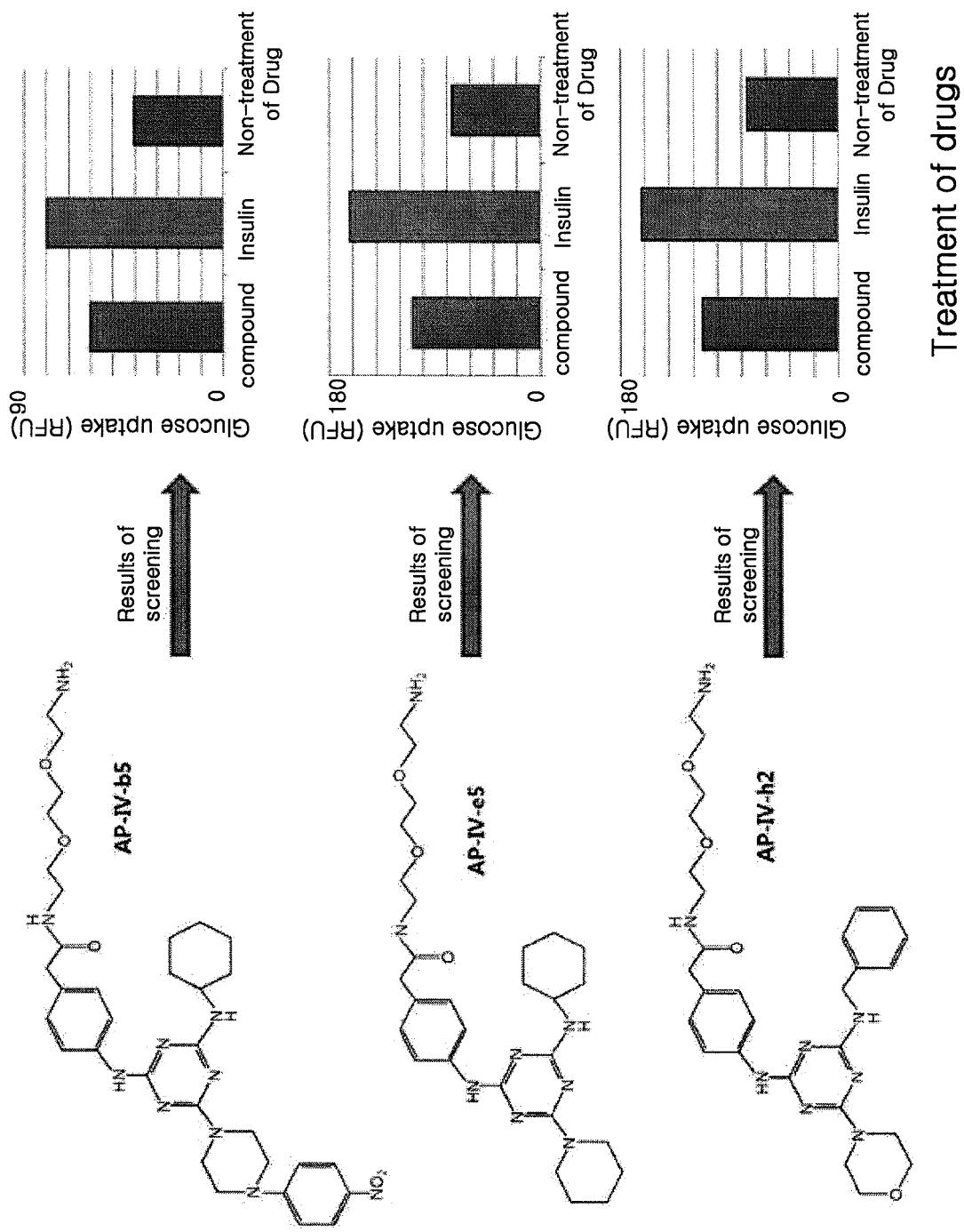
Figure 2F:
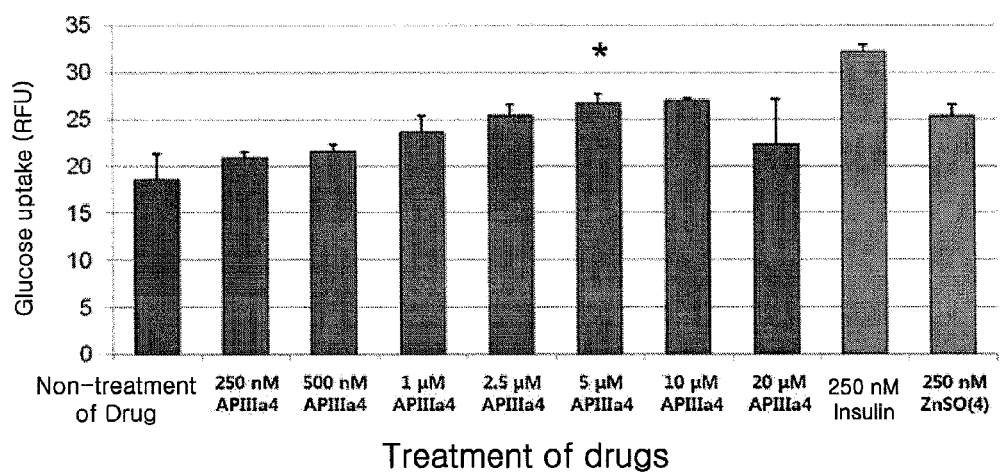
Figure 2G:
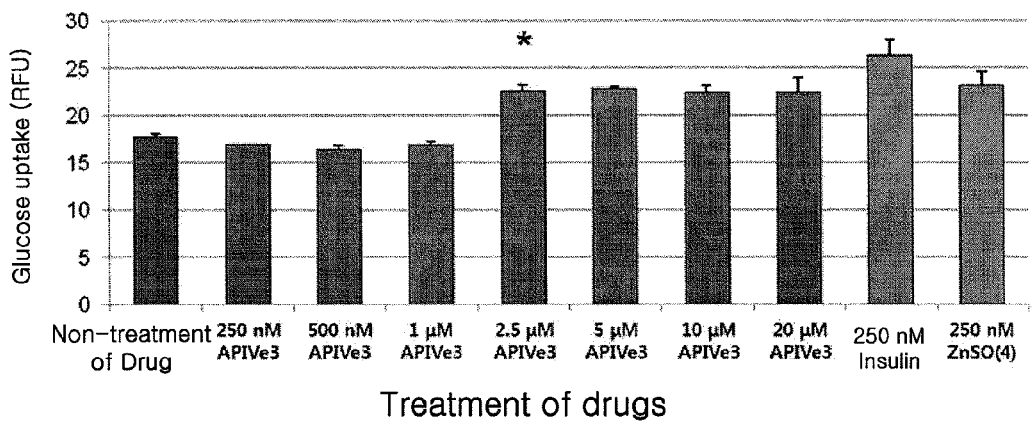
FIG. 2a represents schematic diagram of the novel NBDG-based screening system used to identify new inducers of glucose uptake. The screening protocol can be broken down into nine steps.
Figure 2H:
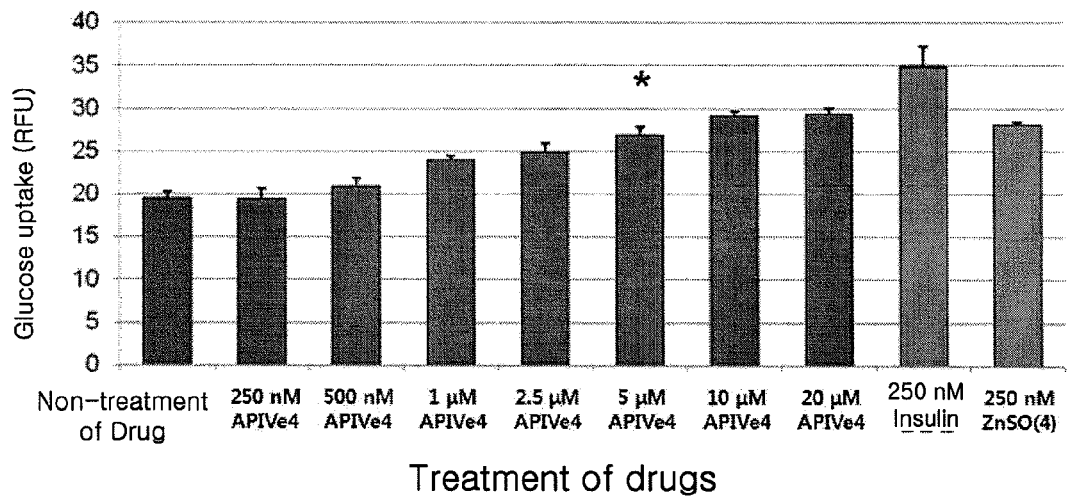
Figure 2I:
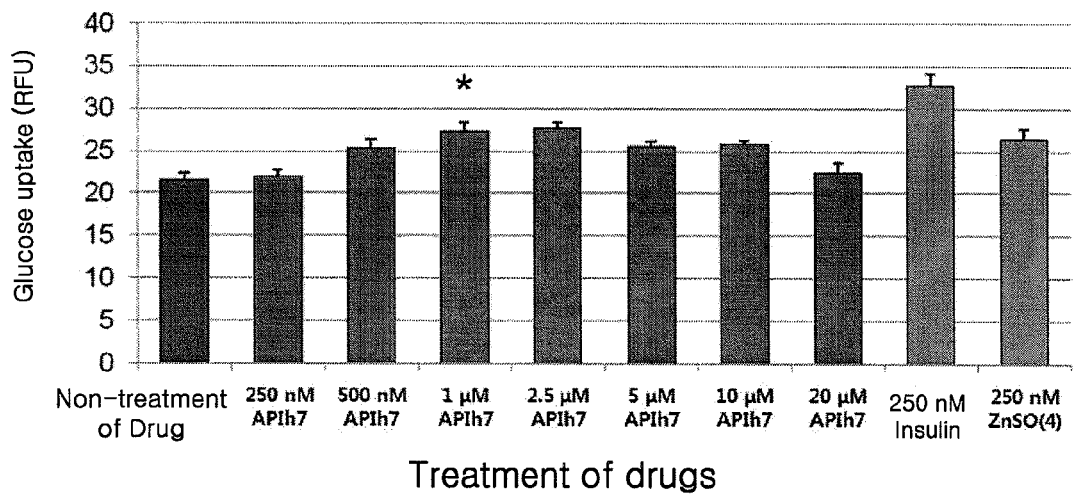
Figure 3A:
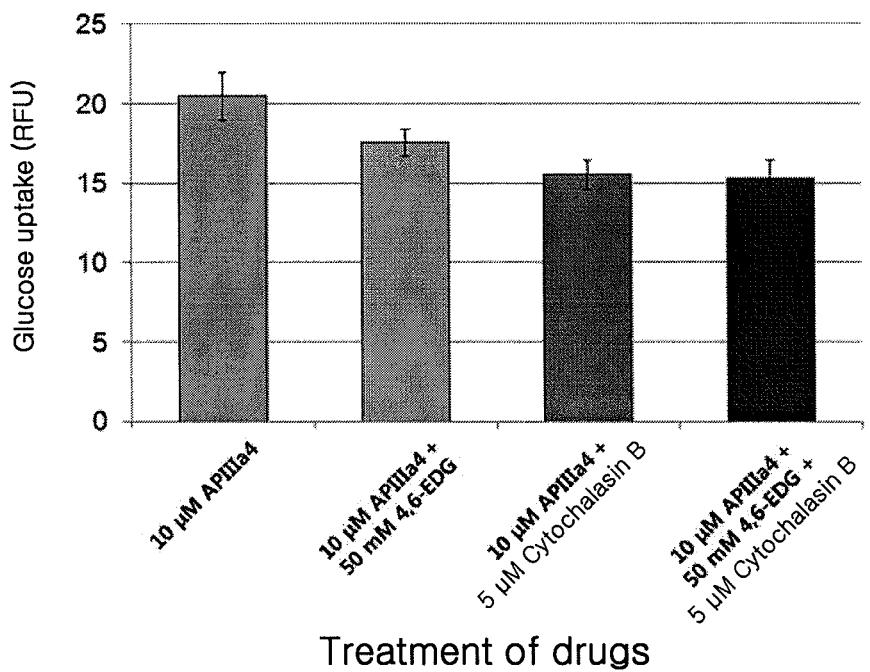
FIG. 3 represents that 6-NBDG-based screening identified four inducers of NBDG uptake which are sensitive to exo- and endofacial inhibitors of GLUT. Compounds AP-III-a4, AP-IV-e3, AP-IV-e4 and AP-I-h7 were compared with the known insulin mimetic compound, zinc sulfate. Error=SD. 3 wells of a 96-well plate/data point. *=P<0.05 compared to compound alone; **=P<0.05 compared to compound plus 50 mM 4,6-EDG. Data is representative of three independent experiments.
Figure 3B:
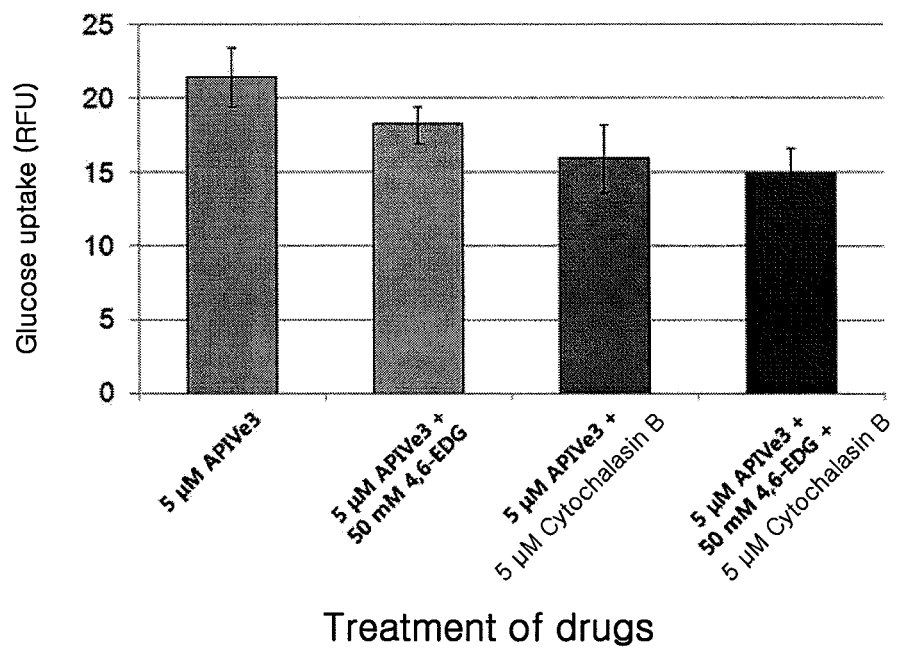
Figure 3C:
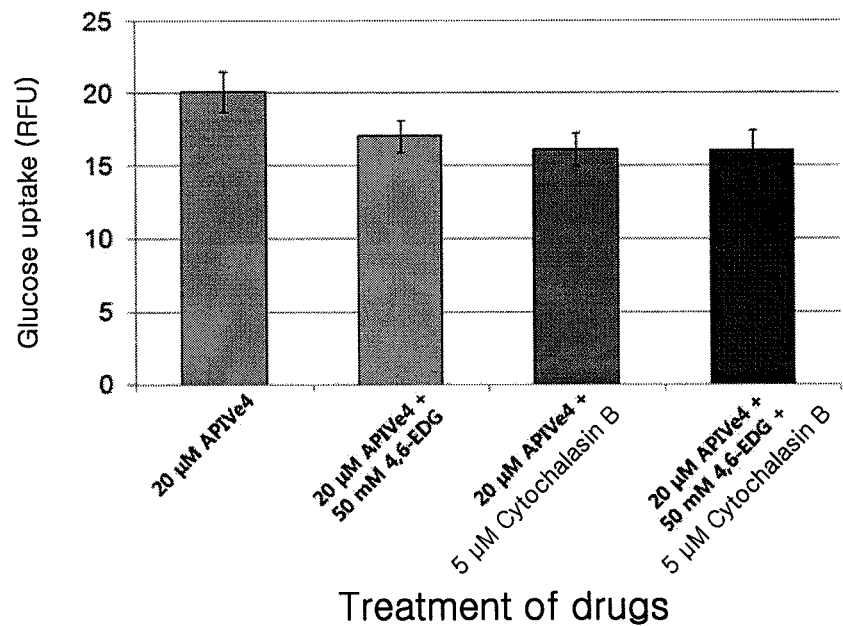
Figure 3D:
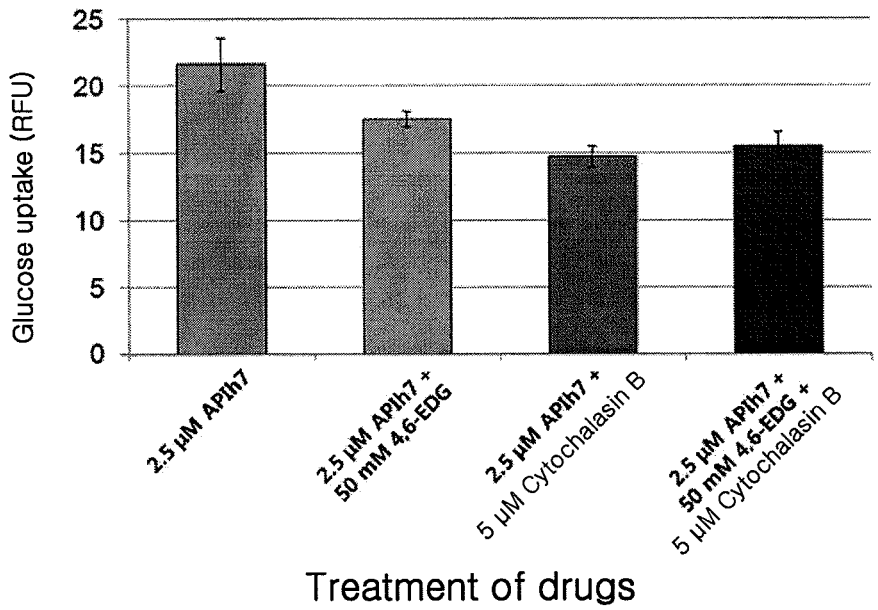
Figure 3E:
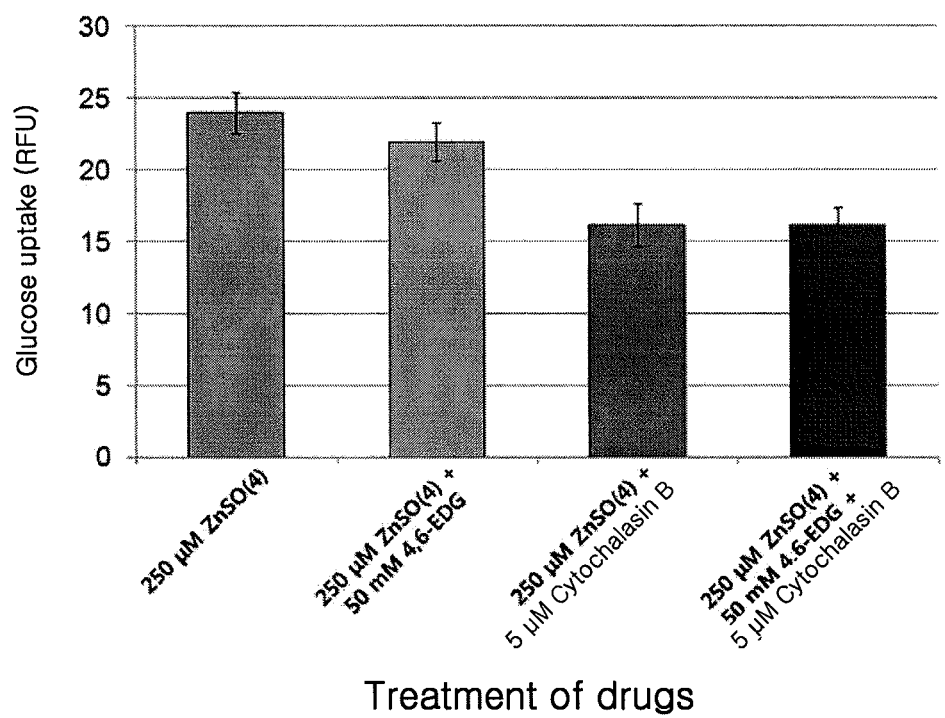

Based on these results, this protocol was then modified to establish a screening protocol using a 96-well culture plate format, differentiated 3T3-L1 adipocytes and 20 µM 6-NBDG treatment (described schematically in Results section FIG. 2a); making it more cost effective and amenable to high-throughput screening applications.

To test the NBDG-based screening system, a combinatorial chemical library of 576 triazine-based small molecules was screened at a concentration of 5 µM. The combinatorial library was provided by Professor Young-Tae Chang, Department of Chemistry, National University of Singapore.

Detection of Apoptosis or Necrosis

3T3-L1 pre-adipocytes were cultured to confluence in 24-well plates and induced to differentiate into adipocytes. The induction of apoptosis was detected using the Apo-TRACE™ Apoptotic Cell Staining Kit (Sigma-Aldrich, SL, USA), which employs a fluorescent compound that responds to alterations in plasma membrane potential and phospholipid scrambling, which are hallmarks of apoptotic cells. Apoptotic cells were visualized by microscopy under UV illumination (Olympus IX81, Japan) equipped with MetaMorph 7.5 image capture software (Molecular Devices, CA, USA)). Images were processed with Photoshop CS4 software (Adobe Systems Incorporated, CA, USA). Apoptosis was quantified by fluorescent microplate reader analysis of cell lysate.

Necrosis was detected by the ability of cells to exclude the dye, trypan blue. 3T3-L1 adipocytes were cultured to confluence in 6-well plates and treated with drug. Adipocytes were then harvested by trpsinization and resuspended in 1 mL PBS. A 50 µL aliquot was taken and stained with an equal volume of 0.4% trypan blue solution (Sigma, SL, USA). Cells that could not exclude dye were classified as necrotic and quantified using a hemocytometer.

Free Fatty Acid Release Assay

Epinephrine-stimulated free fatty acid (FFA) release from adipocytes was measured using the Free Fatty Acid Quantification Kit (Biovision, CA, USA), following the method previously described[13]. Confluent 3T3-L1 adipocytes in a 24 well plate were cultured for 3 h in serum-free culture media. Adipocytes were then treated with 10 µM epinephrine dissolved in saline to induce FFA addition of release. Drug of interest was added 10 min before the addition of epinephrine. Cell lysate was collected and 50 µL of the organic phase was used for assay. Palmitic acid was used to generate the standard curve.

Commercial Glucose Content Assay

For comparison and validation of our new screening based on NBDG uptake, we used a commercial, enzyme-based glucose assay provided by Biovision Inc., CA, USA. 3T3-L1 adipocytes were seeded at $5 \times 10^4$ cells/well in a 96-well culture plate. 24 h later, culture media was changed and adipocytes were cultured in serum-free low glucose DMEM for 3 h prior to drug treatment. Cells were lysed with 100 µL Cell Lytic M (Sigma-Aldrich, SL, USA) and 50 µL lysate was used for assay.

Monocyte-Endothelial Cell Adhesion Assay

The adhesion of mouse inflammatory peritoneal (IP) exudate macrophages to endothelial cell monlayers was carried out as previously described.[14] Briefly, endothelial cells were cultured to confluence in 6-well culture plates and treated with drug with or without high glucose (30 mM for 48 h) culture media. THP-1 human monocytes ($2 \times 10^4$ cells/mL) were added to the monolayers and incubated for 30 min at 37° C. The unbound cells were washed three times with serum-free RPMI-1640 medium, and the total number of adherent cells was counted in four randomly selected optical fields per well (100× magnification; Olympus microscope CKX41, Japan; microscopic images were captured with a DigiEye 330 digital camera (Dewinter, India) and Biowizard 4.3 software (Dewinter, India)). Images were processed with Photoshop CS4 software (Adobe Systems Incorporated, CA, USA).

Western Blot Analysis

Proteins were separated by 10% SDS-PAGE and transferred onto 0.2 µM nitrocellulose (Bio-Rad, CA, USA). Densitometry was carried out using TINA 2.10e software (Catholic University Medical College (GmBH), Germany).

Statistical Analysis of Data

The Mann-Whitney U test (TalkStats software; Jelsoft Enterprises Ltd., UK) was used to determine significance. A P value of less than 0.05 was considered to be significant.

Result

NBDG can be Used to Detect Insulin-Stimulated Glucose Uptake, Insulin Sensitizing Compounds and Glucose Transporter Type 4 Inhibitors in Adipocytes Previous research on the use of NBDG to detect insulin-stimulated glucose uptake has produced conflicting results.[10,11] In addition, NBDG has not yet been used to detect insulin sensitizing compounds or insulin mimetic agents in cell-based screening. Therefore, our first experiment was to test whether NBDG could be used to detect insulin-stimulated glucose uptake in cells cultured in a 96 well-plate format (FIG. 1a). The effect of an insulin-sensitizing compound, rosiglitazone, was also tested. Three cell lines were chosen for this test (Huh7 hepatocytes, C2C12 myoblasts and 3T3-L1 pre-adipocytes), which represent the major body tissue types that are sensitive to the action of insulin (liver, muscle and fat). 3T3-L1 adipocytes showed the largest increase in 2-NBDG uptake after insulin treatment, which was significantly greater than 2-NBDG uptake in Huh7 hepatocytes, C2C12 myoblasts, C2C12 myotubes and 3T3-L1 pre-adipocytes. Treatment with rosiglitazone for 24 h increased the degree of insulin-stimulated 2-NBDG uptake in 3T3-L1 adipocytes.

Figure 1B:
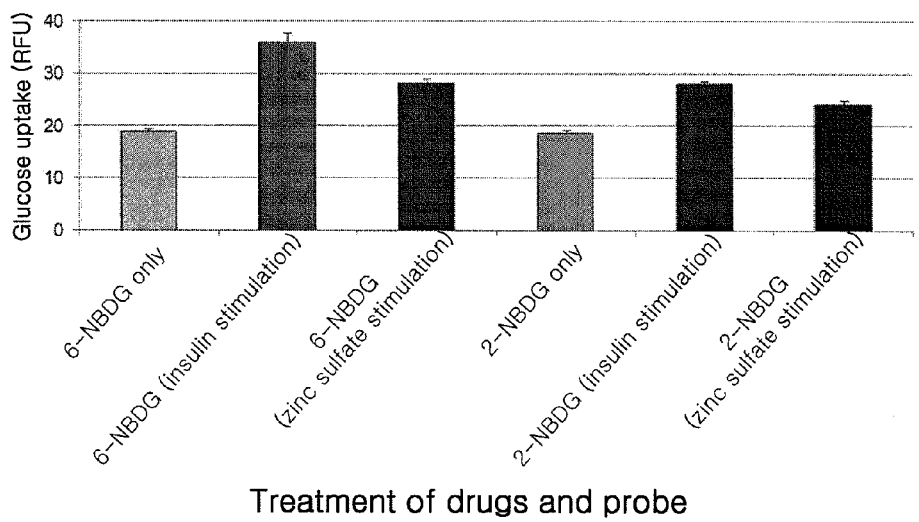
FIG. 1b represents that 6-NBDG uptake is greater than 2-NBDG uptake in 3T3-L1 adipocytes after treatment with 100 nM insulin or the insulin mimetic zinc sulfate (250 µM). Error=SD. 3 wells of a 96-well plate/data point. *=P<0.05 compared to 2-NBDG uptake alone; #=P<0.05 compared to 6-NBDG uptake alone.
Figure 1C:
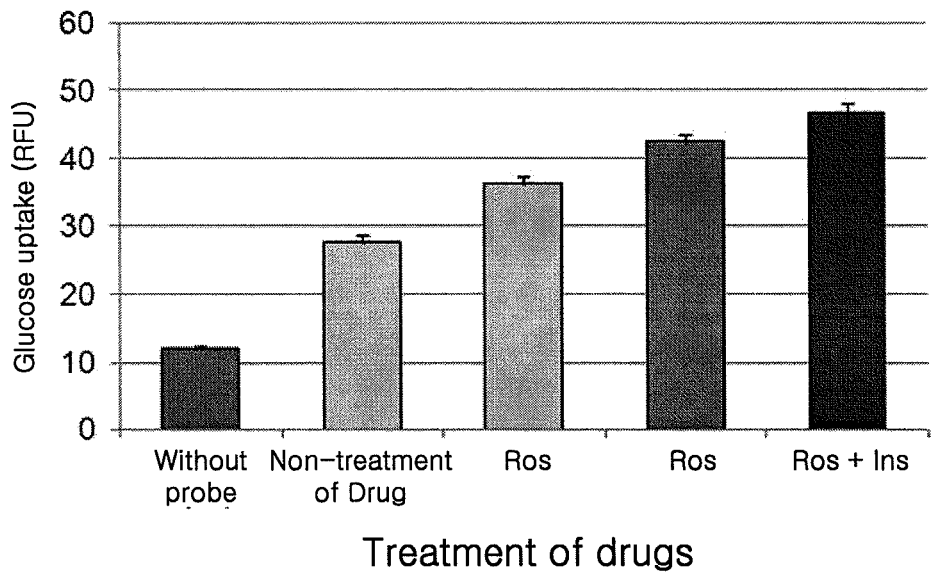
FIG. 1c represents that 6-NBDG uptake in adipocytes is sensitive to insulin and the insulin-sensitizing compound, rosiglitazone. Ros=1 µM rosiglitazone; Ins=100 nM insulin. *=P<0.05 compared to no probe; **=P<0.05 compared to 6-NBDG alone. #=P<0.05 compared to rosiglitazone; ##=P<0.05 compared to insulin. Error=SD. 3 wells of a 96-well plate/data point.

6-NBDG is a non-metabolizable analogue of 2-NBDG. Therefore, the inventors compared insulin-stimulated uptake of these analogues in 3T3-L1 adipocytes (FIG. 1b). It was found that 6-NBDG produced a greater fluorescent signal than 2-NBDG. A similar result was obtained using the insulin mimic, zinc sulfate. Therefore, 6-NBDG was used for further studies. 6-NBDG uptake was also sensitive to the insulin-sensitizing compound, rosiglitazone, similar to the result obtained using 2-NBDG (FIG. 1c).

Figure 1D:
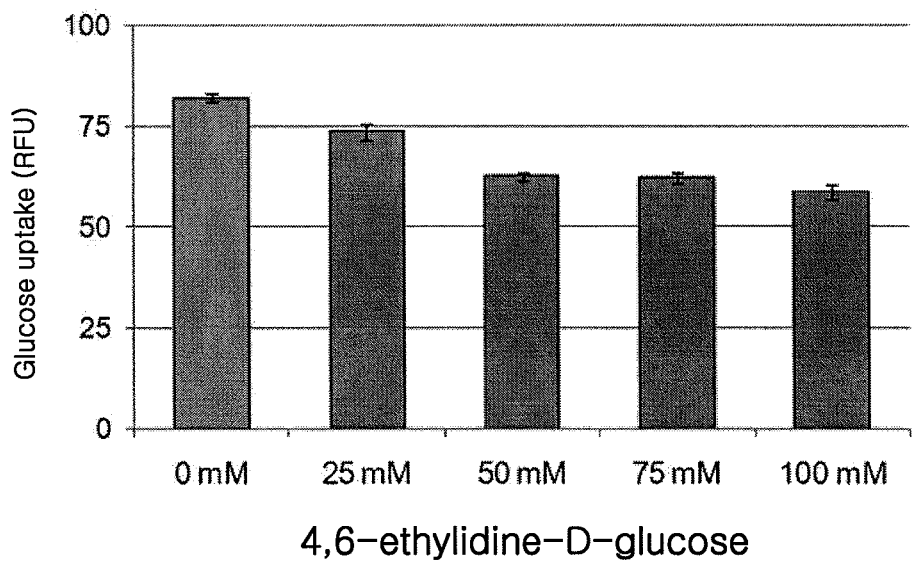
FIG. 1d represents that 100 nM nsulin-stimulated 6-NBDG uptake in adipocytes is inhibited by the GLUT inhibitors 4,6-EDG and cytochalasin B (3 h pre-treatment with inhibitors). *=P<0.05 compared to no treatment. Error=SD. 3 wells of a 96-well plate/data point. Data in FIGS. 1a-1e is representative of three independent experiments.
Figure 1E:
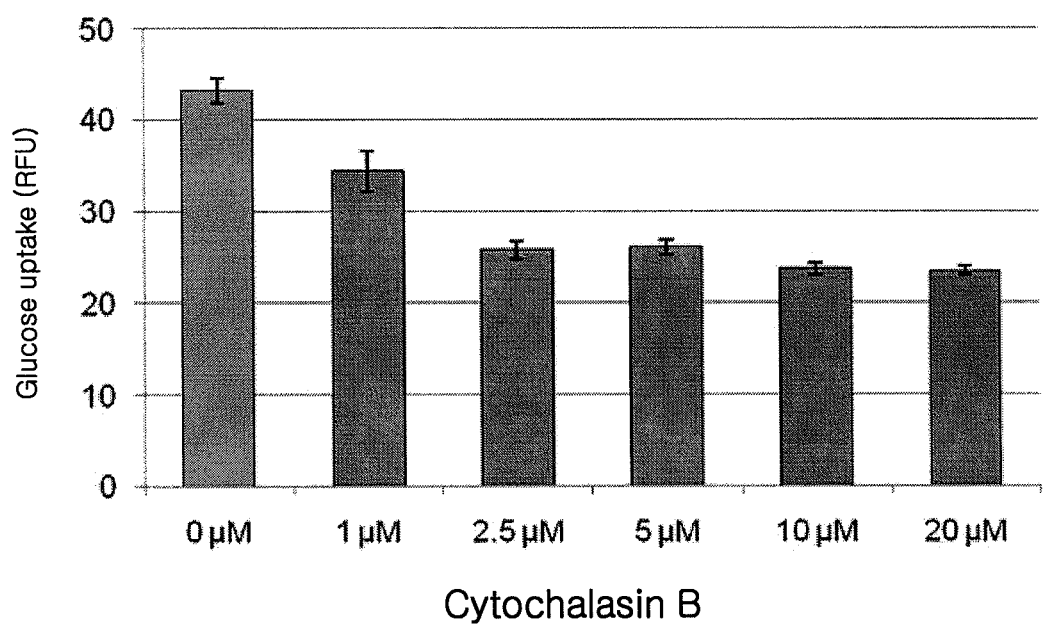

Glucose transporter type 4 (GLUT4) is the insulin-regulated glucose transporter in adipose tissue and striated muscle.[15] To further ensure that 6-NBDG uptake is due to insulin-stimulated activation of GLUT4, we tested the effect of two inhibitors of GLUT4, cytochalasin B and 4,6-ethylidine-D-glucose (4,6-EDG). Both inhibitors of GLUT 4 reduced insulin-stimulated uptake of 6-NBDG (FIGS. 1d-1e).

Development and Use of a Cell-Based Screening System to Detect Novel Insulin Mimetics Data in FIGS. 1a-1e indicates that 6-NBDG uptake in 3T3-L1 adipocytes is sensitive to insulin, insulin mimetics, insulin sensitizing compounds and glucose transporter type 4 inhibitors. Thus, we developed a novel screening protocol for novel insulin mimetics, based on mircoplate reader detection of 20 µM 6-NBDG uptake in 3T3-L1 adipocytes cultured in a 96-well plate format (shown schematically FIG. 2a). To test if this screening protocol could detect new insulin mimetic compounds, a combinatorial chemical library of 576 triazine-based small molecules was screened. The triazine library was selected because of structural similarity to purine and pyrimidine, which are active in biological systems (e.g. triazolopyrimidines (8-azapurines) have applications in cancer and viral chemotherapy).[16] Five 'hit' compounds were found to induce a significant increase in 6-NBDG uptake (≥25% increase compared to untreated adipocytes). In addition, two compounds were found to cause a significant decrease in the basal level of 6-NBDG uptake in untreated dipocytes (≥25% decrease). Further testing of the purified compounds confirmed that four of the 'hit' compounds can increase NBDG uptake in adipocytes (designated AP-III-a4, AP-IV-e3, AP-IV-e4 and AP-I-h7), while two compounds can reduce NBDG uptake (designated AP-III-a12 and AP-I-d5) (FIGS. 2f-2i).

To further confirm that these hit compounds can increase NBDG uptake in adipocytes, the effect of the GLUT4 inhibitors, cytochalasin B and 4,6-EDG, was tested. Treatment with either GLUT4 inhibitor reduced NBDG uptake, in a similar manner to the known insulin mimetic, zinc sulfate (FIG. 3).

Figure 4A:
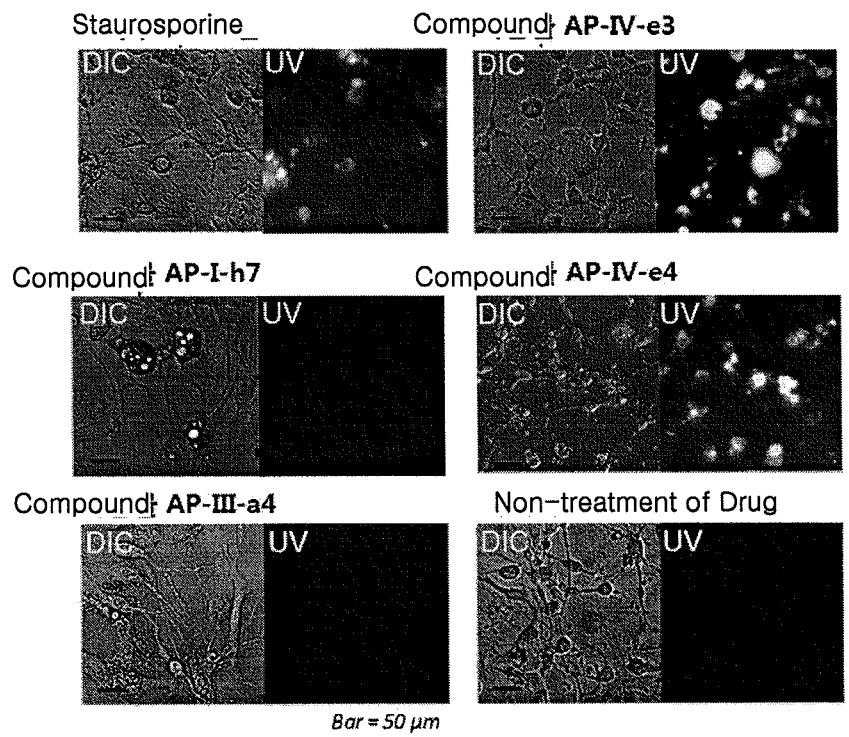
FIG. 4a represents that treatment of 3T3-L1 adipocytes with 5 µM compounds AP-IV-e3 or AP-IV-e4 for 24 hrs induced apoptosis, as detected by the Apo-TRACE™ fluorescent compound which responds to alterations in plasma membrane potential and phospholipid scrambling. In contrast, the compounds AP-III-a4 and AP-I-h7 did not induce apoptosis. Staurosporine treatment (500 nM for 24 hrs) was used as a positive control for the induction of apoptosis.
Figure 4B:
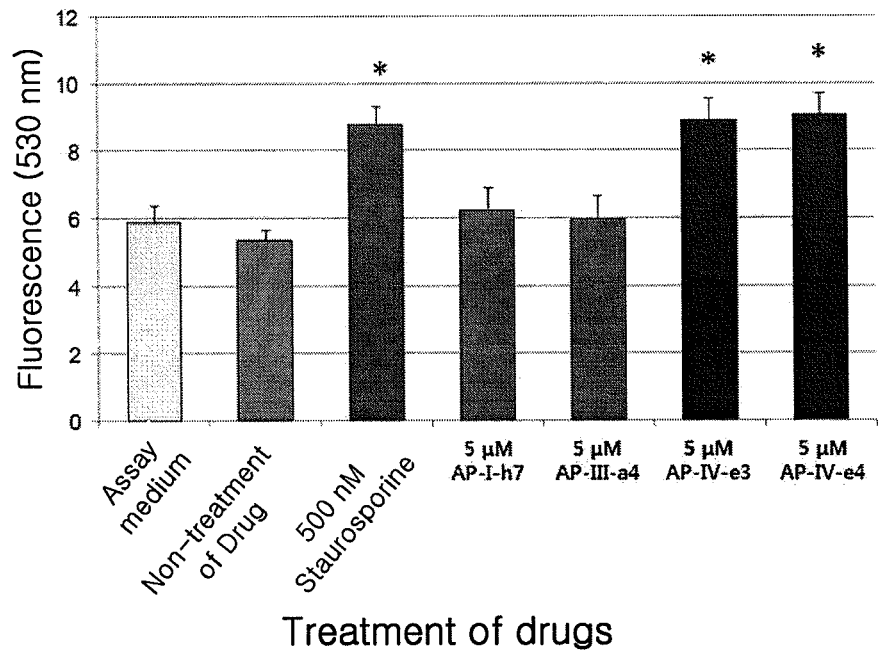
FIG. 4b represents fluorescent microplate reader quantification of the induction of apoptosis by compounds AP-IV-e3 or AP-IV-e4 in3T3-L1 adipocytes (24 h treatment with compound). Error=SD. 3 wells of a 24-well plate/data point. *=P<0.05 compared to no treatment.
Figure 4C:
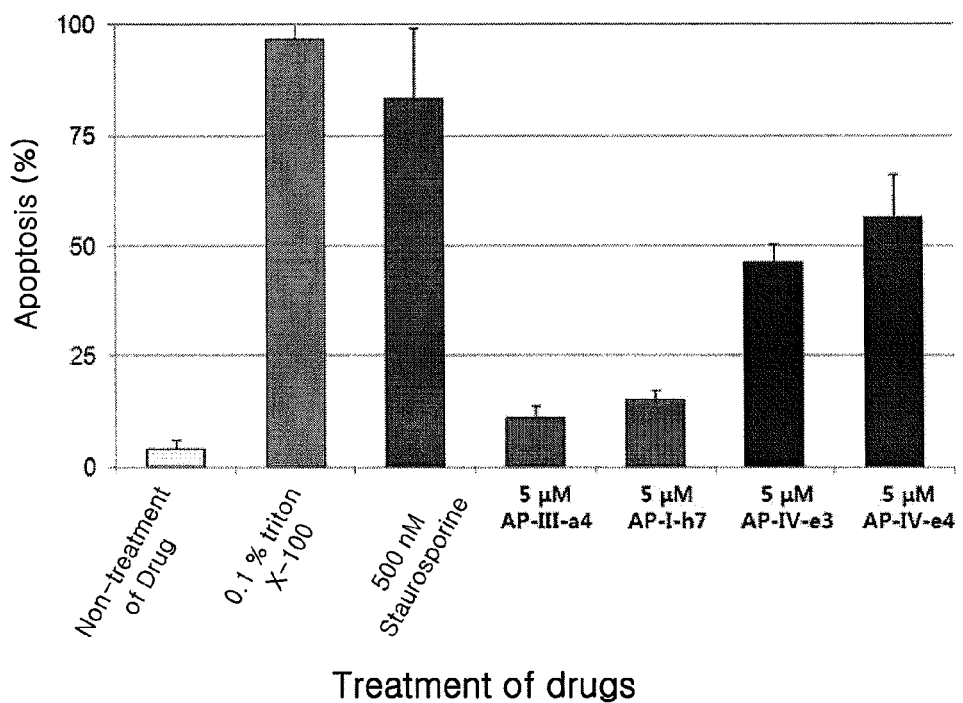
FIG. 4c represents that compounds AP-IV-e3 or AP-IV-e4 also induced cell death in 3T3-L1 adipocytes 24 h after treatment. Staurosporine treatment (500 nM for 24 h) or triton x-100 treatment (0.1% in PBS for 1 h) was used as positive controls. Error=SD. *=P<0.05 compared to no treatment; **=P<0.05 compared to compounds AP-IV-e3 or AP-IV-e4; #=P<0.05 compared to compounds AP-III-a4 and AP-I-h7; Data is representative of three independent experiments.

Further Analyses to Confirm that 'Hit' Compounds Identified by NBDG-Based Screening are True Insulin Mimetic Agents Novel NBDG-based screening system for discovering insulin mimetic agents in the present invention identified four compounds from a combinatorial chemical library of 576 triazine-based small molecules (FIG. 2). However, a number of cellular mechanisms can induce glucose uptake independently of insulin, such as cell stress and apoptosis.[17] Therefore, we assessed cytotoxicty in adipocytes after treatment with these four 'hit' compounds, AP-III-a4, AP-IV-e3, AP-IV-e4 and AP-I-h7. It was found that two of the hit compounds, AP-IV-e3 and AP-IV-e4, induced apoptosis in adipocytes (FIGS. 4a and 4b). In addition, compounds AP-IV-e3 and AP-IV-e4 induced cell death as determined by cellular exclusion of the dye, trypan blue (FIG. 4c). Therefore, compounds AP-IV-e3 and AP-IV-e4 were discounted from further study.

Figure 5A:
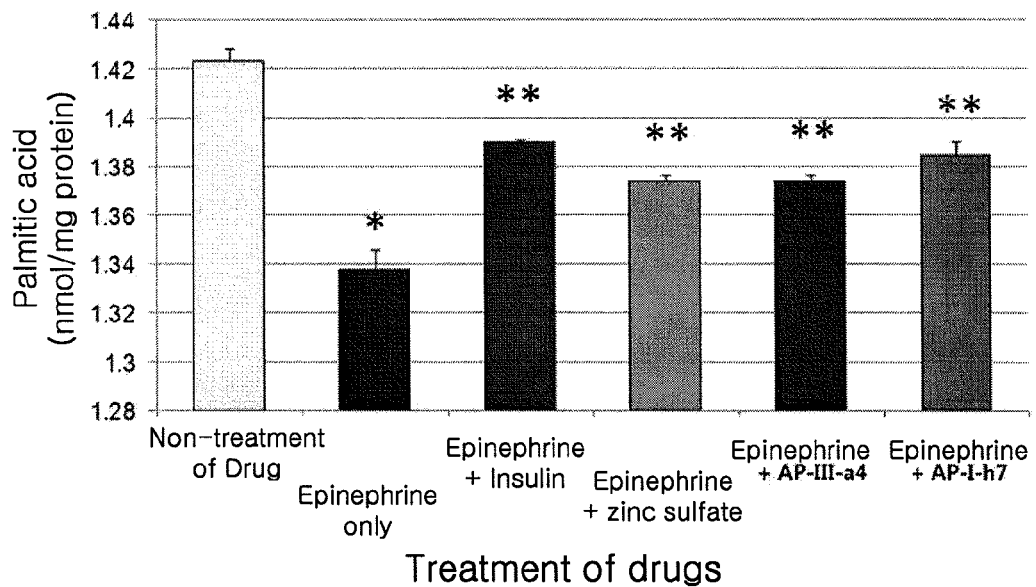
FIG. 5a represents that compounds AP-III-a4 and AP-I-h7, identified by 6-NBDG-based cellular screening, are confirmed insulin mimetic compounds, as shown by their ability to inhibit 10 µM epinephrine-mediated FFA release from adipocytes. 5 µM compounds AP-III-a4 and AP-I-h7 performed as well as 250 µM zinc sulfate, widely studied insulin mimetic. 100 nM insulin was used as the positive control. Error=SD. *=P<0.05 compared to no treatment; **=P<0.05 compared to epinephrine alone.
Figure 5B:
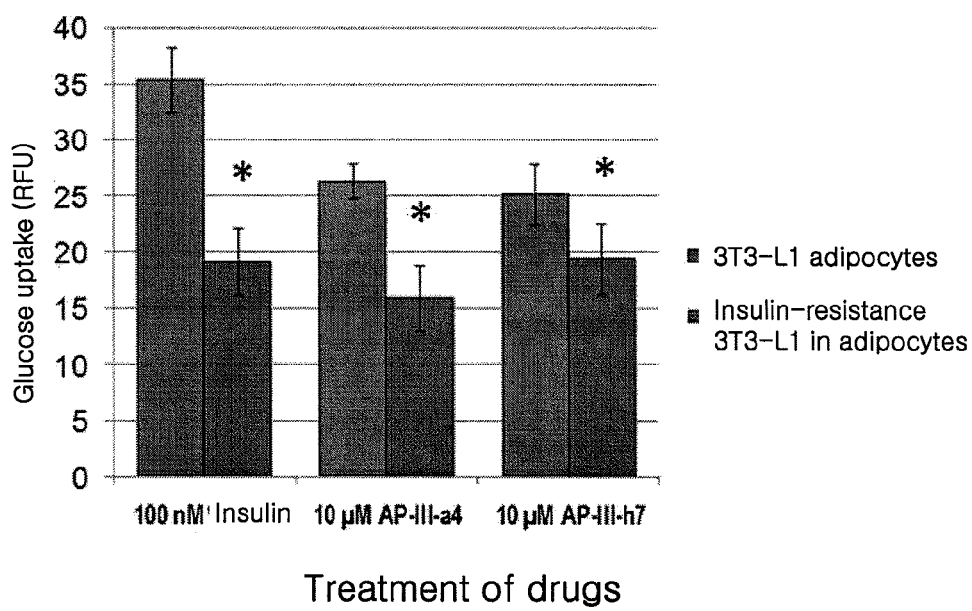
FIG. 5b represents that NBDG uptake in adipocytes treated with compounds AP-III-a4 and AP-I-h7 is sensitive to the induction of insulin resistance. The reduction in NBDG uptake in insulin resistant adipocytes was of a similar degree to insulin treatment. Error=SD. *=P<0.05 compared to 3T3-L1 adipocytes in the same treatment group.
Figure 5C:
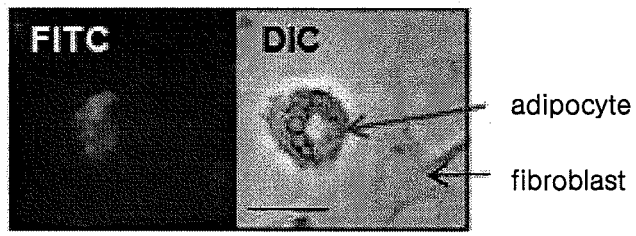
FIG. 5c represents that 6-NBDG uptake after treatment with 10 µM insulin mimetic compounds AP-III-a4 and AP-I-h7 preferentially occurs in adipocytes rather than fibroblasts. Adipocytes express an insulin-sensitive cellular reservoir of GLUT4, whereas the co-cultured undifferentiated 3T3-L1 pre-adipocytes possess fibroblast-like characteristics and are much less responsive to insulin. This finding further confirms that compounds AP-III-a4 and AP-I-h7 are novel insulin mimetics. Data is representative of three independent experiments.
Figure 5C:
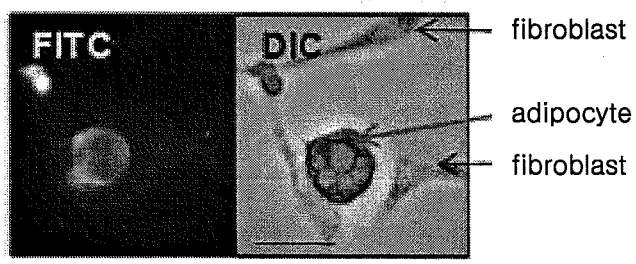
Figure 5C:
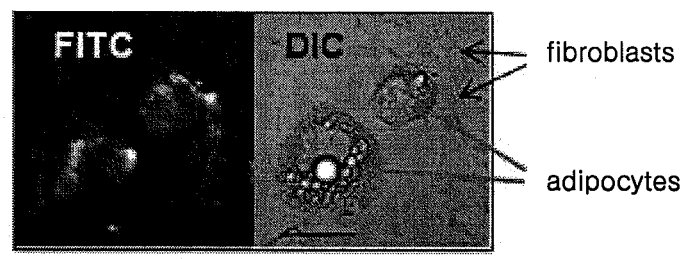
Figure 5C:
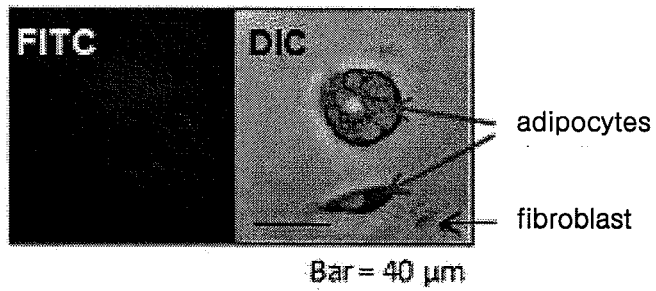

A classic test for validating candidate insulin mimetic compounds is the prevention of epinephrine-stimulated free fatty acid release from adipocytes.[2,18] The candidate insulin mimetic compounds AP-III-a4 and AP-I-h7 could inhibit epinephrine-stimulated free fatty acid release from 3T3-L1 adipocytes (FIG. 5a), confirming that these two triazine-based small molecules represent a new chemical class of insulin mimetics. An interesting further test of these novel insulin mimetics is their sensitivity to insulin resistance in adipocytes, such as in a recent study of the aqueous extract from the Mediterranean coastal herb *Teucrium cubense* Jacq.[19] Using adipocytes that were rendered insulin resistant by long-term culture in the presence of TNF-$\alpha$,[20] it was shown that NBDG uptake induced by compounds AP-III-a4 and AP-I-h7 was sensitive to insulin resistance (FIG. 5b). This result also confirmed that compounds AP-III-a4 and AP-I-h7 are novel insulin mimetics. Adipocytes are sensitive to insulin-stimulated glucose uptake because they increase expression of GLUT4 during differentiation from pre-adipocytes.[21] Fluorescent microscope analysis of NBDG uptake in mixed cultures of adipocytes and pre-adipocytes treated with compounds AP-III-a4 and AP-I-h7 showed that NBDG was preferentially taken up in the adipocytes (FIG. 5c). This result also confirmed that compounds AP-III-a4 and AP-I-h7 stimulate glucose uptake by a biochemical mechanism similar to insulin.

Figure 6A:
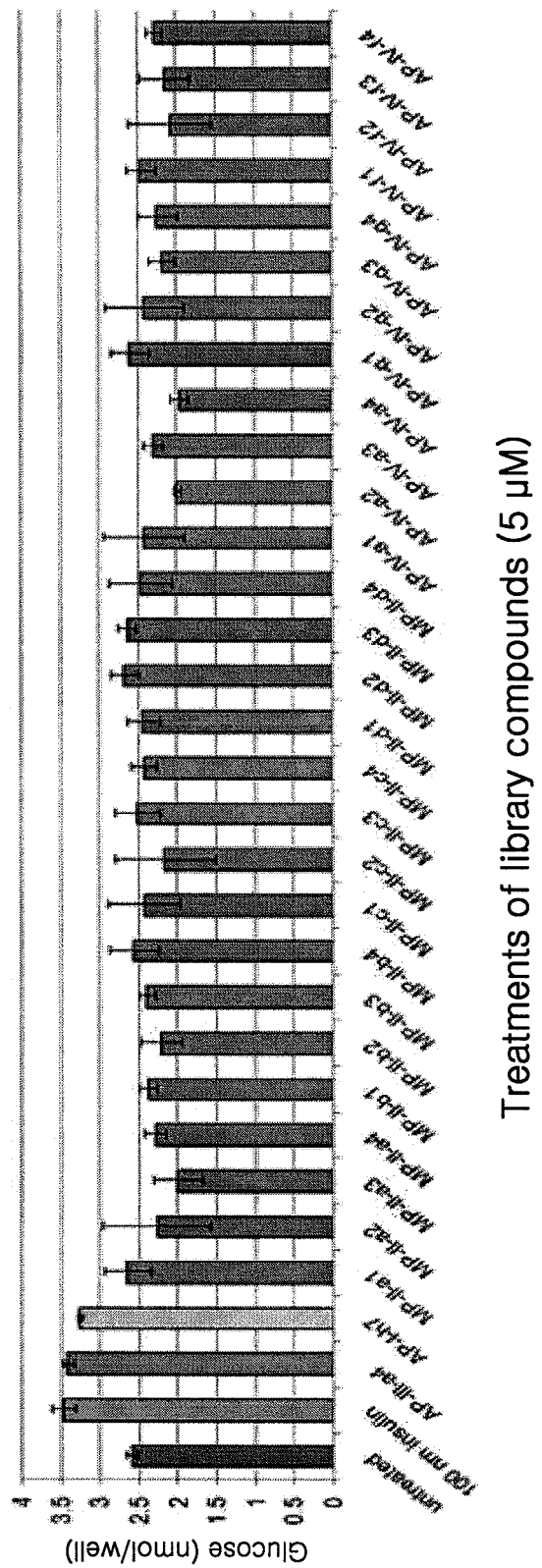
FIG. 6 represents that the present novel 6-NBDG-based screening system for insulin mimetics performed well against a commercial, enzyme-based glucose assay provided by Biovision Inc., CA, USA. A portion of the triazine-based chemical library (including the two newly identified novel insulin mimetic compounds AP-III-a4 and AP-I-h7) was tested in triplicate using this enzyme-based glucose assay (the capacity of the assay was 96 samples). The insulin mimetic compounds AP-III-a4 and AP-I-h7 induced an increase in cellular glucose content in 3T3-L1 adipocytes. Error=SD. Other compounds from the chemical library could not induce an increase in cellular glucose content to the same degree as compounds AP-III-a4 and AP-I-h7. The margin of error obtained using the novel 6-NBDG-based screening system was preferable compared to the margin of error obtained using the commercial, enzyme-based glucose assay.
Figure 6B:
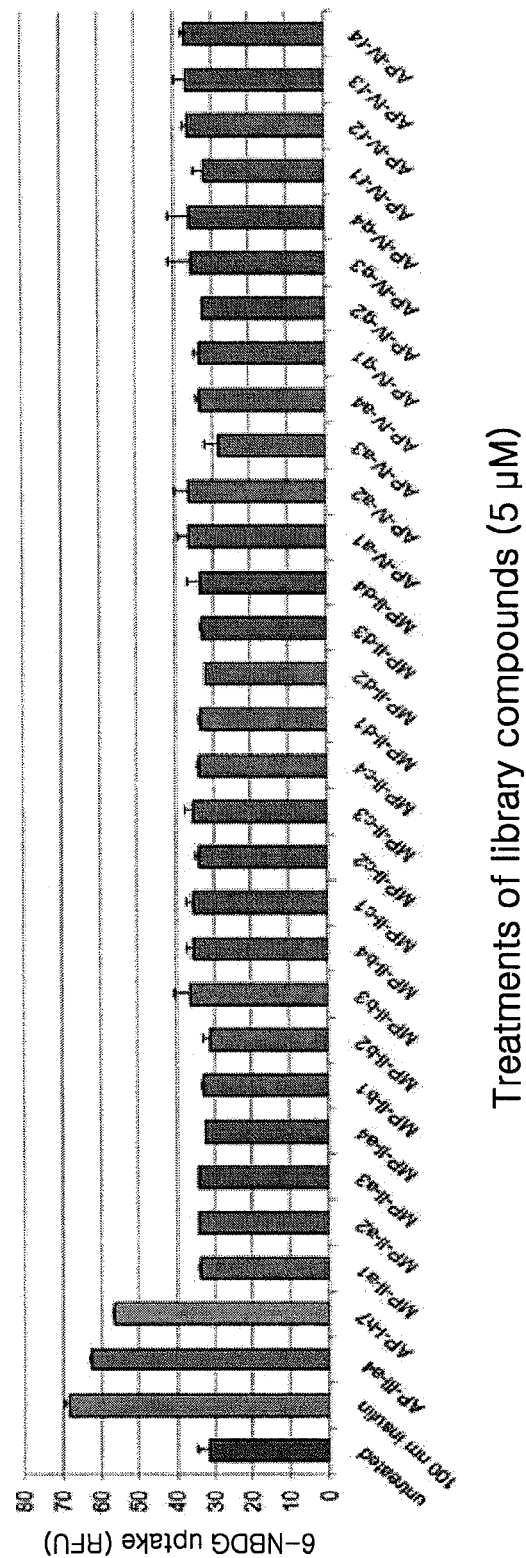

Comparison of 6-NBDG-Based Screening Data with a Commercial Glucose Content Assay To confirm the validity of the novel NBDG screening system used to identify the novel insulin mimetic compounds AP-III-a4 and AP-I-h7, screening results were compared with a commercial enzyme-based assay of glucose content (Biovision, CA, USA). A portion of the triazine-based combinatorial library, including the novel insulin mimetic compounds AP-III-a4 and AP-I-h7, was screened again using this enzyme-based assay (FIG. 6). Treatment of adipocytes with insulin or the novel insulin mimetic compounds AP-III-a4 and AP-I-h7 induced an increase in cellular glucose content; a result which validates the establishment of our novel 6-NBDG-based screening protocol to identify novel insulin mimetics. In addition, the corresponding 6-NBDG-based screening data was found to be more rigorous than the enzyme-based assay; there was less standard deviation error between library compounds and a proportionally greater signal from the 'hit' compounds.

Figure 7:
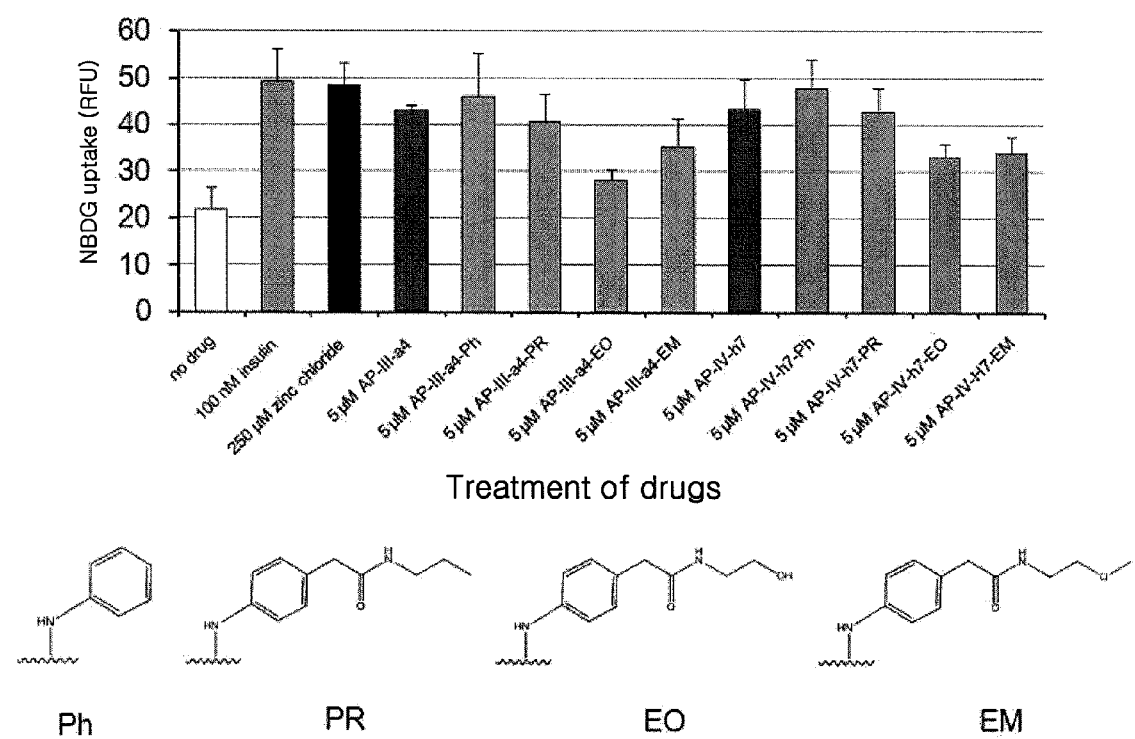
FIG. 7 represents effects of a linker for activities of novel compounds identified in the present invention. The liker moiety of the triazine-based insulin mimetic compounds AP-III-a4 and AP-I-h7 in the present invention was prepared in various structures: the length of the linker become shorter in sequence of EM, EO, PR and Ph. The effects of total five different compounds per one compound were compared. Although it is a difference of degree, treatments of all kind of compounds increased an uptake of glucose analogues into cells. Error=SD.

In the meantime, to more elaborately verify effective moieties of AP-III-a4 and AP-I-h7 as insulin mimetic compounds, a linker moiety of each compound was prepared in four (4) structures and the cellular glucose content in adipocytes was measured (FIG. 7). As a result, it was shown that only the triazine-based compound represented by Formula I induced an increase in cellular glucose content.

Figure 8A:
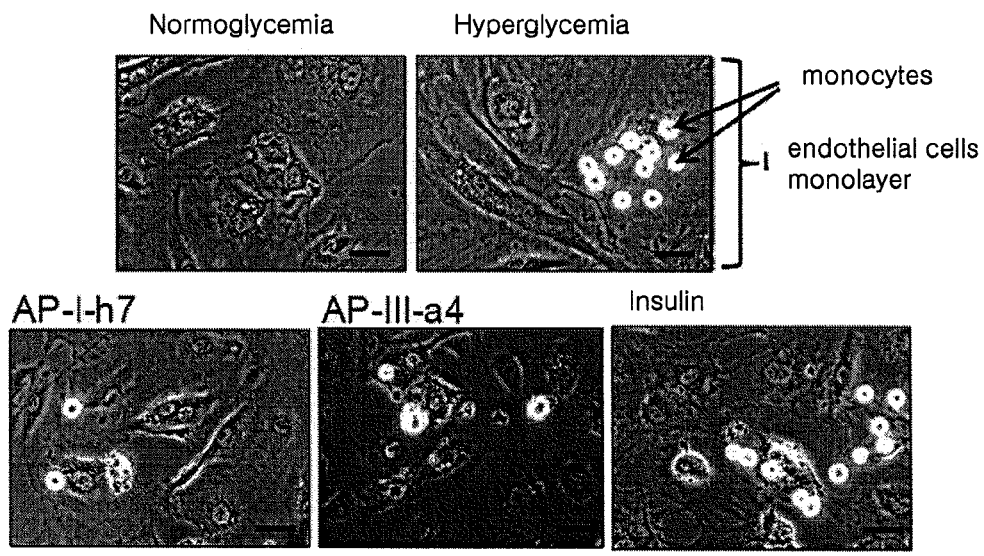
FIG. 8a represents that treatment of human aortic endothelial cells (HAEC) with insulin mimetic compounds AP-III-a4 or AP-I-h7 reduced monocyte adhesion induced by hyperglycemia. HAEC were exposed to hyperglycemia (30 mM glucose) for days and treated with 5 µM compounds AP-III-a4 or AP-I-h7 or 100 nM insulin for 3 hrs prior to addition of THP-1 monocytes.
Figure 8B:
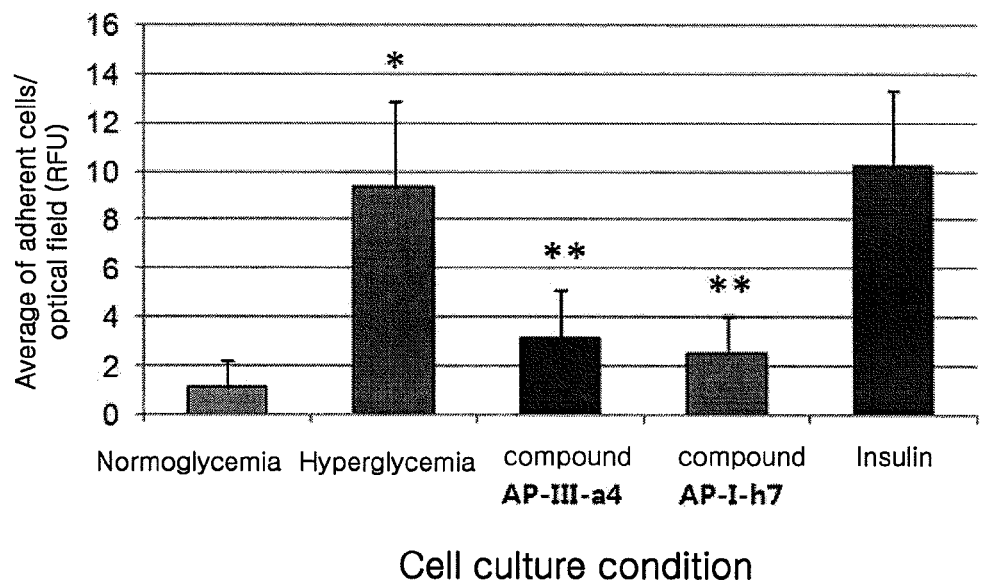
FIG. 8b represents that the inhibitory effect of insulin mimetic compounds AP-III-a4 or AP-I-h7 on monocyte binding to HAEC in the hyperglycemic condition was quantified by cell counting under light microscopy. Error=SD. *=P<0.05 compared to normoglycemia; **=P<0.05 compared to hyperglycemia.
Figure 8C:
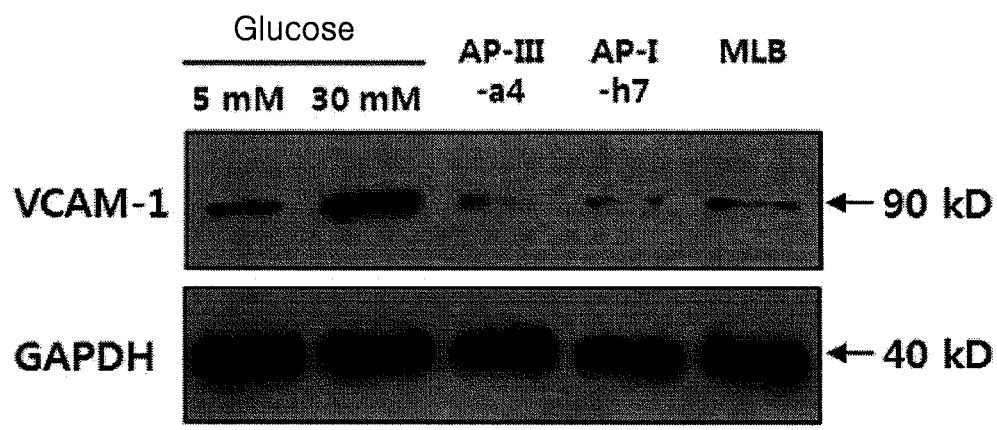
FIGS. 8c and 8d represent that insulin mimetic compounds AP-III-a4 or AP-I-h7 reduced the expression of VCAM-1 in HAEC exposed to hyperglycemia. The level of inhibition of VCAM-1 expression compared well with magnesium lithospermate B, an anti-diabetic agent with known beneficial secondary effects against diabetic secondary complications[23]. Data is representative of three independent experiments. 5 mM glucose=normoglycemia; 30 mM glucose=hyperglycemia (5 days treatment); AP-III-a4=hyperglycemia (5 days treatment) and 24 hrs treatment with 5 µM AP-III-a4; AP-I-h7=hyperglycemia (5 days treatment) and 24 hrs treatment with 5 µM AP-III-a4; MLB=hyperglycemia (5 days treatment) and 48 hrs treatment with 50 µM magnesium lithospermate B.
Figure 8D:
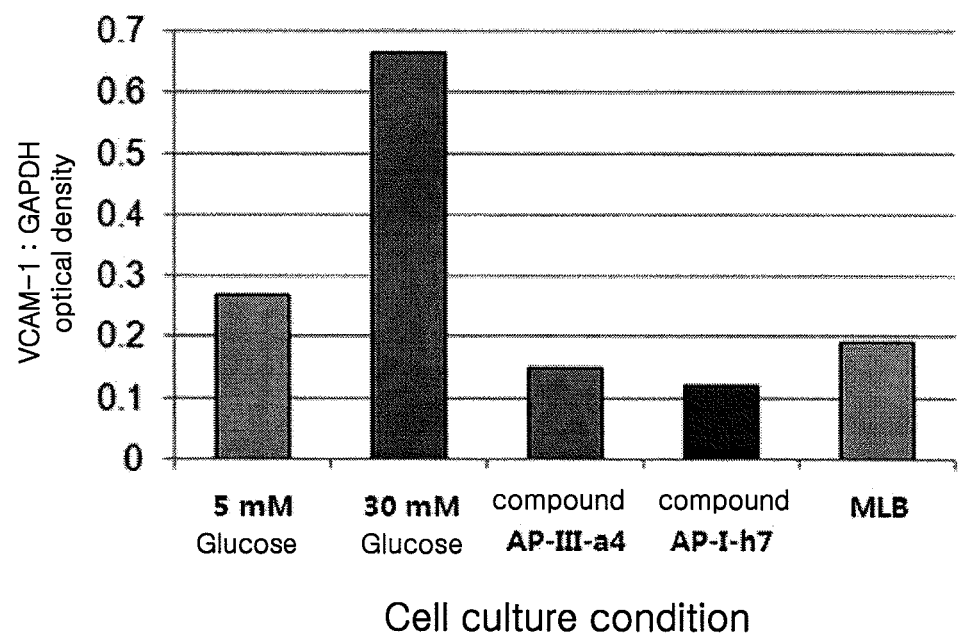

Novel Insulin Mimetic Compounds AP-III-a4 and AP-I-h7 Induce an Additional, Anti-Inflammatory Effect Current research in the development of new therapeutics for diabetes focuses on agents that produce additional, beneficial secondary effects on cell function in hyperglycemic conditions.[22,23] Therefore, we measured the effect of novel insulin mimetic compounds AP-III-a4 and AP-I-h7 on monocyte-endothelial cell adhesion, which is a key primary step in the development of diabetic secondary complications, such as atherosclerosis.[24] It was found that treatment of human aortic endothelial cells with insulin mimetic compounds AP-III-a4 and AP-I-h7 decreased monocyte adhesion in hyperglycemic conditions (FIGS. 8a and 8b). Vascular cell adhesion molecule-1 (VCAM-1) is a key intracellular receptor mediating monocyte-endothelial adhesion[25]. Insulin mimetic compounds AP-III-a4 and AP-I-h7 decreased VCAM-1 upregulation in human aortic endothelial cells cultured in hyperglycemic conditions (FIG. 8c). Insulin has been shown not to inhibit adhesion molecule expression in endothelial cells.[26] The inhibitory effect of compounds AP-III-a4 and AP-I-h7 on VCAM-1 expression compared favorably with the natural product magnesium lithospermate B (MLB), an anti-diabetic agent with known beneficial secondary effects.[23] These results suggests that novel insulin mimetic compounds AP-III-a4 and AP-I-h7 are interesting candidates for future, expanded studies as potential anti-diabetic therapeutics.

Discussion

Due to the rising number of people with diabetes, there is a need to develop efficient, cost-effective and safe screening protocols to identify new insulin mimetics that can be developed into new therapeutics or probes to understand diabetic mechanisms. 2- and 6-NBDG were initially developed as fluorescent probes to monitor glucose uptake in live cells and the study of GLUT1 receptor kinetics, respectively.[7,8] The use of NBDG by the research community to monitor glucose uptake has steadily increased. A PubMed search (U.S. National Library of Medicine National Institutes of Health) retrieved 54 hits for NBDG since 1985, with 10 hits for the years 2009/2010. However, recent research using NBDG has focused more on the monitoring of glycolysis in cancer cells, rather than diabetes-related research.[27,28]

Our data presented in the present invention shows that NBDG can be used to rapidly identify new candidate insulin mimetic compounds using cell-based screening. Previous studies that attempted to use NBDG in this manner have produced conflicting results[10-12] and there is no published report describing the use of NBDG to discover novel insulin mimetics. Our novel screening system based on NBDG is based on 3T3-L1 adipocytes, which we have shown are more sensitive to insulin-sensitive NBDG uptake than hepatocytes or differentiated muscle syncytia, even though liver and skeletal muscle are the main targets of insulin in the body (FIG. 1a). This finding is consistent with previous reports that the uptake of radio-labelled glucose is approximately five-fold lower in differentiated skeletal muscle culture compared to differentiated adipocytes, even though both cell types increase expression of GLUT4 during differentiation.[29] Our result also contrasts with a previous report that NBDG can be used to detect insulin-stimulated glucose uptake in monocytes[10], even though the level of GLUT4 expression is lower than in adipocytes. However, it should be noted that flow cytometry was used to analyze glucose uptake in monocytes, while our screening study employed a fluorescent microplate reader (for experimental convenience compared to flow cytometry). However, it should be noted that other studies of NBDG uptake using flow cytometry failed to detect insulin-stimulated glucose uptake in hepatocytes or skeletal muscle cultures.[11]

The two analogues of NBDG, 2-NBDG and 6-NBDG, were compared in our study and it was found that 6-NBDG produced a greater fluorescent signal using our screening protocol (FIG. 1b). This is consistent with the metabolic fate of NBDG upon cellular uptake. 2-NBDG enters the glycolytic pathway and is converted to a fluorescent c-6 phospho-derivative, 2-NBDG 6-phosphate, after which it is decomposed to non-fluorescent forms.[8,12] However, 6-NBDG is non-metabolizable, which could explain why it produced a greater fluorescent signal in our screening protocol. This non-metabolizable feature of 6-NBDG also allowed us to reduce the concentration required for screening, from 100 μM (the typically used concentration) down to 20 μM, increasing the cost-effectiveness of our screening assay. Also, our novel NBDG-based assay was also sensitive to commonly prescribed insulin sensitizing drugs, such as rosiglitazone, and known inhibitors of GLUT4, such as cytochalasin B and 4,6-EDG (FIGS. 1c and 1d), validating our screening assay as a tool to detect novel insulin mimetics. Very recent research has suggested that the exofacial GLUT inhibitor 4,6-EDG should be used for inhibition of NBDG uptake, because NBDG kinetic studies demonstrated an approximately 100-fold greater affinity for GLUT compared to free glucose, while passage of NBDG through GLUT was reduced compared to free glucose[9]. However, our screening system also shows sensitivity to cytochalsin B inhibition (an endofacial GLUT inhibitor), presumably because cytochalasin B can efficiently inhibit the passage of NBDG that does enter the cell over the time-course of our assay. The concentrations of 4,6-EDG and cytochalasin B used in our study to inhibit NBDG uptake are in line with a previous report of NBDG kinetic validation[9].

The screening of a combinatorial chemical library of 576 triazine-based small molecules identified five 'hit' compounds that produced ≥25% increase in 6-NBDG uptake compared to untreated adipocytes. This corresponds to a hit ratio of 0.868% (to three decimal places). Re-testing of the putative hits confirmed that four compounds from the chemical library could induce NBDG uptake, meaning that 0.694% of the compounds were confirmed 'hits' that respond to GLUT4 inhibitors (FIG. 2b-2f and FIG. 3). This ratio of hits is useful because it falls into the range where sufficient hits compounds are detected for further study, without producing an excessive number of false positive 'hits'.

A potential problem with any screening system to identify novel insulin mimetics is the influence of additional cellular mechanisms that could induce glucose uptake independently of insulin, such as cell stress and apoptosis[17]. Therefore, we carried out additional tests to check that the hit compounds did not induce apoptosis or necrosis. Two of the four confirmed hit compounds were shown to induce apoptosis and discounted from further study. Thus we recommend that cytotoxicty should be checked as a first step in the analysis of the hit compounds. Testing for cytotoxicty would also be beneficial for determining if the candidate insulin mimetic compounds possess therapeutic potential.

Our chemical library used to validate this novel NBDG-based cellular screening system allows us to introduce two new insulin mimetic compounds, AP-III-a4 and AP-I-h7, which are based on the triazine molecular scaffold. This scaffold has structural similarity to purine and pyrimidine, which are active in biological systems, e.g. triazolopyrimidines (8-azapurines) have applications in cancer and viral chemotherapy[16]. The inventors and other research groups have shown that screening of this chemical library has produced other interesting compounds, such as inhibitors of the F1F0 ATPase and the mitochondrial chaperone, prohibitin[30,31]. Compounds AP-III-a4 and AP-I-h7 from this library were shown to be true insulin mimetics by their ability to inhibit epinephrine-mediated FFA release from adipocytes; to a similar degree as the widely studied insulin mimetic, zinc sulfate (FIG. 5a). This test is a standard experimental method to confirm insulin mimetic activity[2,18] and we have further confirmed that compounds AP-III-a4 and AP-I-h7 were true insulin mimetic agents by their sensitivity to TNF-α induced insulin resistance (FIG. 5b). The present invention are favourable because the concentrations of AP-III-a4 and AP-I-h7 required to produce insulin mimetic activity in adipocytes is markedly lower than the widely studied synthetic insulin mimetics, zinc(II) complexes and vanadium compounds (5 μM compared to 250 μM-500 μM)[2,18]. In addition, current research into potential new drugs for treating diabetes has shifted focus to the identification of agents that produce beneficial, secondary effects in cells sensitive to hyperglycemia, such as activation of cellular antioxidant response pathways or anti-inflammatory effects[23,32]. The inventors have shown that novel insulin mimetic compounds AP-III-a4 and AP-I-h7 also possess anti-inflammatory activity, as evidenced by their inhibition of monocyte adhesion to endothelial cells in hyperglycemic conditions and the inhibition of hyperglycemia-stimulated upregulation of VCAM-1 expression in endothelial cells (FIG. 8). Increased monocyte-endothelial adhesion and VCAM-1 upregulation are important precursors of diabetes-associated atherosclerosis[24,25]. Previously, insulin treatment has been shown to have no inhibitory effect on monocyte-endothelial adhesion[26]. Therefore, novel insulin mimetic compounds AP-III-a4 and AP-I-h7 are attractive candidate compounds for further study as agents that can directly treat the insulin deficiency in diabetes as well as reducing the progression of debilitating diabetes-associated complications.

In summary, we have described the development of a new screening system that can identify novel insulin mimetic agents and is based on the uptake of NBDG. This screening system is convenient, cost effective and rapid, in addition to performing well against a commercial assay of glucose content (FIG. 6). Two new insulin mimetic compounds were identified by screening a well-characterized chemical library of 576 triazine-based small molecules. These results validate the development of NBDG-based screening systems for discovering new anti-diabetic agents.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCE

1. G. E. Umpierrez, A. Palacio and D. Smiley, *Am J Med,* 2007, 120, 563-567.
2. M. Nishide, Y. Yoshikawa, E. U. Yoshikawa, K. Matsumoto, H. Sakurai and N. M. Kajiwara, *Chem Pharm Bull (Tokyo),* 2008, 56, 1181-1183.
3. B. Zhang, G. Salituro, D. Szalkowski, Z. Li, Y. Zhang, I. Royo, D. Vilella, M. T. Diez, F. Pelaez, C. Ruby, R. L. Kendall, X. Mao, P. Griffin, J. Calaycay, J. R. Zierath, J. V. Heck, R. G. Smith and D. E. Moller, *Science,* 1999, 284, 974-977.
4. W. L. Li, H. C. Zheng, J. Bukuru and N. De Kimpe, *J Ethnopharmacol,* 2004, 92, 1-21.
5. N. Malviya, S. Jain and S. Malviya, *Acta Pol Pharm,* 2010, 67, 113-118.
6. L. F. Barros, M. Young, J. Saklatvala and S. A. Baldwin, *J Physiol,* 1997, 504(Pt3), 517-525.
7. L. Speizer, R. Haugland and H. Kutchai, *Biochim Biophys Acta,* 1985, 815, 75-84.
8. K. Yoshioka, H. Takahashi, T. Homma, M. Saito, K. B. Oh, Y. Nemoto and H. Matsuoka, *Biochim Biophys Acta,* 1996, 1289, 5-9.
9. L. F. Barros, C. X. Bittner, A. Loaiza, I. Ruminot, V. Larenas, H. Moldenhauer, C. Oyarzun and M. Alvarez, *J Neurochem,* 2009, 109 Suppl1, 94-100.

10. G. Dimitriadis, E. Maratou, E. Boutati, K. Psarra, C. Papasteriades and S. A. Raptis, *Cytometry A*, 2005, 64, 27-33.
11. C. Zou, Y. Wang and Z. Shen, *J Biochem Biophys Methods*, 2005, 64, 207-215.
12. F. Leira, M. C. Louzao, J. M. Vieites, L. M. Botana and M. R. Vieytes, *Toxicol In Vitro*, 2002, 16, 267-273.
13. M. Nakai, F. Sekiguchi, M. Obata, C. Ohtsuki, Y. Adachi, H. Sakurai, C. Orvig, D. Rehder and S. Yano, *J Inorg Biochem*, 2005, 99, 1275-1282.
14. J. Kim, K. H. Nam, S. O. Kim, J. H. Choi, H. C. Kim, S. D. Yang, J. H. Kang, Y. H. Ryu, G. T. Oh and S. E. Yoo, *FASEB J*, 2004, 18, 714-716.
15. D. E. James, M. Strube and M. Mueckler, *Nature*, 1989, 338, 83-87.
16. W. B. Parker, J. A. Secrist, 3rd and W. R. Waud, *Curr Opin Investig Drugs*, 2004, 5, 592-596.
17. S. A. Baldwin, L. F. Barros, M. Griffiths, J. Ingram, E. C. Robbins, A. J. Streets and J. Saklatvala, *Biochem Soc Trans*, 1997, 25, 954-958.
18. K. Kawabe, Y. Yoshikawa, Y. Adachi and H. Sakurai, *Life Sci*, 2006, 78, 2860-2866.
19. A. J. Alonso-Castro, R. Zapata-Bustos, J. Romo-Yanez, P. Camarillo-Ledesma, M. Gomez-Sanchez and L. A. Salazar-Olivo, *J Ethnopharmacol*, 2010, 127, 1-6.
20. G. S. Hotamisligil, D. L. Murray, L. N. Choy and B. M. Spiegelman, *Proc Natl Acad Sci USA*, 1994, 91, 4854-4858.
21. A. Garcia de Herreros and M. J. Birnbaum, *J Biol Chem*, 1989, 264, 19994-19999.
22. G. E. Mann, B. Bonacasa, T. Ishii and R. C. Siow, *Curr Opin Pharmacol*, 2009, 9, 139-145.
23. S. H. Kim, M. Choi, Y. Lee, Y. O. Kim, D. S. Ahn, Y. H. Kim, E. S. Kang, E. J. Lee, M. Jung, J. W. Cho, D. R. Williams and H. C. Lee, *Cardiovasc Res* 2010, DOI 10.1093/cvr/cvq089.
24. R. J. Esper, J. O. Vilarino, R. A. Machado and A. Paragano, *Adv Cardiol*, 2008, 45, 17-43.
25. K. Yonekawa and J. M. Harlan, *J Leukoc Biol*, 2005, 77, 129-140.
26. G. Li, E. J. Barrett, S. H. Ko, W. Cao and Z. Liu, *Endocrinology*, 2009, 150, 3475-3482.
27. S. R. Millon, J. H. Ostrander, J. Q. Brown, A. Raheja, V. L. Seewaldt and N. Ramanujam, *Breast Cancer Res Treat*, 2010, DOI:10.1007/s10549-010-0884-1.
28. N. Nitin, A. L. Carlson, T. Muldoon, A. K. El-Naggar, A. Gillenwater and R. Richards-Kortum, *Int J Cancer*, 2009, 124, 2634-2642.
29. A. Ueyama, K. L. Yaworsky, Q. Wang, Y. Ebina and A. Klip, *Am J Physiol*, 1999, 277, E572-578.
30. D. Williams, D. W. Jung, S. M. Khersonsky, N. Heidary, Y. T. Chang and S. J. Orlow, *Chem Biol*, 2004, 11, 1251-1259.
31. J. R. Snyder, A. Hall, L. Ni-Komatsu, S. M. Khersonsky, Y. T. Chang and S. J. Orlow, *Chem Biol*, 2005, 12, 477-484.
32. R. Kleemann, L. Verschuren, B. J. de Rooij, J. Lindeman, M. M. de Maat, A. J. Szalai, H. M. Princen and T. Kooistra, *Blood*, 2004, 103, 4188-4194.

What is claimed is:

1. A method for treating diabetes, comprising administering to a subject in need thereof a pharmaceutically effective amount of a triazine-based compound represented by the following Formula I:

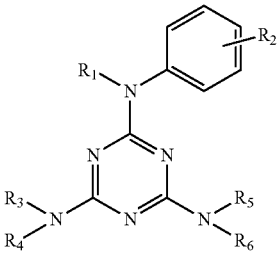

wherein, $R_1$ is H;

$R_2$ is —$(CH_2)_q$—(CONH)—$C_{1-5}$ straight or branched alkyl (q is an integer of 1 to 2), —$(CH_2)_q$—(CONH)—$C_{1-5}$ straight or branched alkyl alcohol (q is an integer of 1 to 2), —$(CH_2)_q$—(CONH)—$[(CH_2)_m$—$O]_n$—$(CH_2)_p$—$NH_2$ (each of m, n and p is an integer of 1 to 5, respectively, and q is an integer of 1 to 2), —$(CH_2)_q$—(CONH)—$[(CH_2)_m$—$O]_n$—$CH_3$ (each of m and n is an integer of 1 to 5, respectively, and q is an integer of 1 to 2) or —$(CH_2)_q$—(CONH)—$[(CH_2)_m$—$O]_n$—$(CH_2)_p$—$CH_3$ (each of m, n and p is an integer of 1 to 5, respectively, and q is an integer of 1 to 2);

$R_3$ is straight $C_1$-$C_5$ alkyl, $C_4$-$C_{20}$ alkyl cycloalkyl or $C_7$-$C_{16}$ aralkyl; aryl group of the aralkyl may be substituted with halogen;

$R_4$ is H, or $R_3$ and $R_4$ are linked to each other to form $C_3$-$C_{10}$ heterocycle in which $C_3$-$C_{10}$ heterocycle optionally comprises oxygen or nitrogen as a heteroatom, wherein the heteroatom is optionally substituted with $C_6$-$C_{10}$ aryl or $C_6$-$C_{10}$ aryl having a halogen or a nitro substituent;

$R_5$ is $C_7$-$C_{16}$ aralkyl or $C_4$-$C_{15}$ alkyl cycloalkyl; and $R_6$ is H; and, the triazine-based compound represented by the Formula I does not comprise compounds represented by the following Formulae 19 and 20:

[Formula 19]

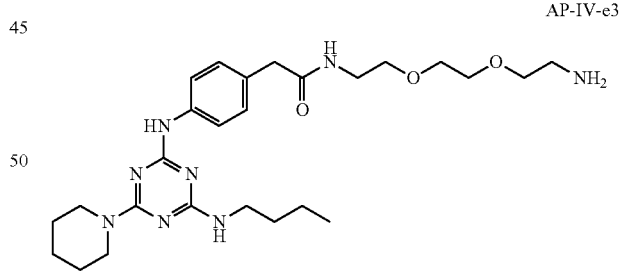

AP-IV-e3

[Formula 20]

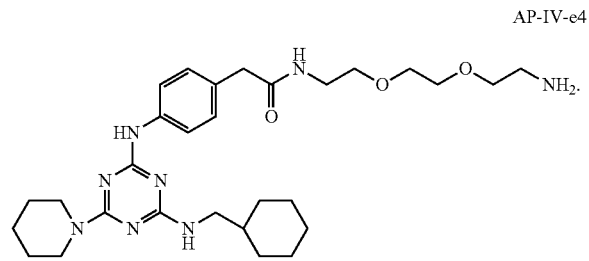

AP-IV-e4

2. The method according to claim 1, wherein the triazine-based compound comprises compounds represented by the following Formulae 1-12:
[Formula 1]
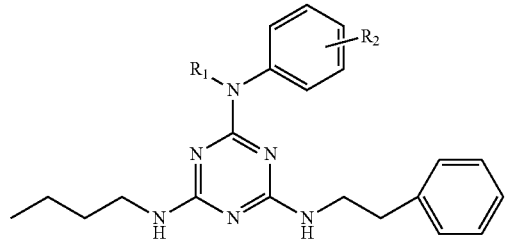
[Formula 2]
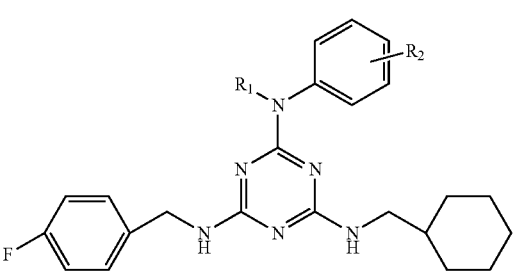
[Formula 3]
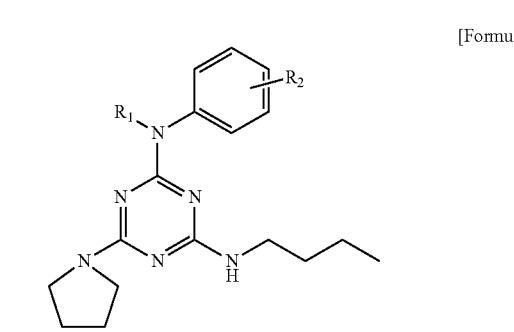
[Formula 4]
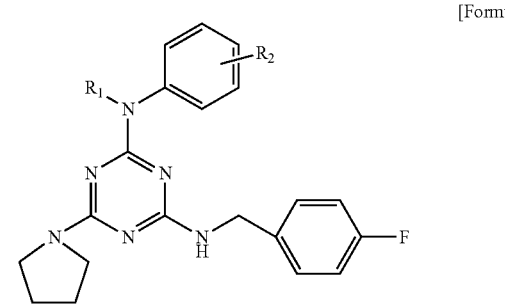
[Formula 5]
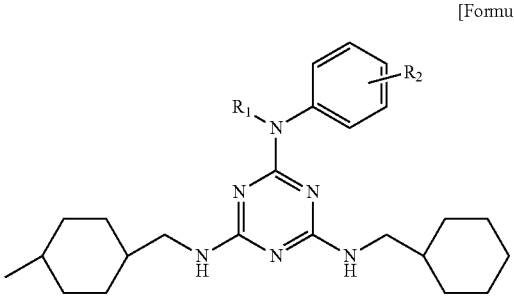
[Formula 6]
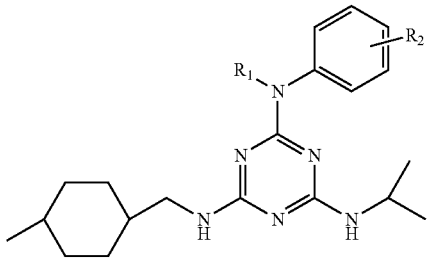
[Formula 7]
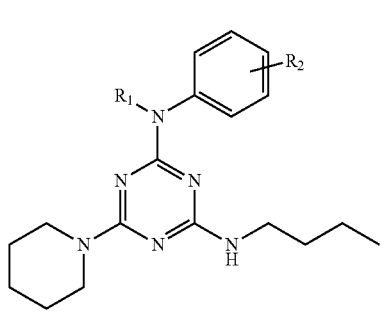
[Formula 8]
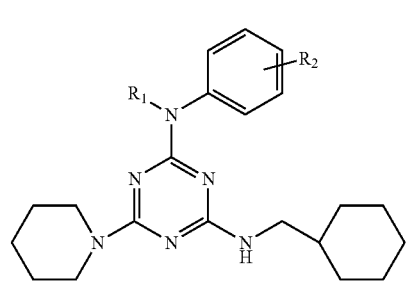
[Formula 9]
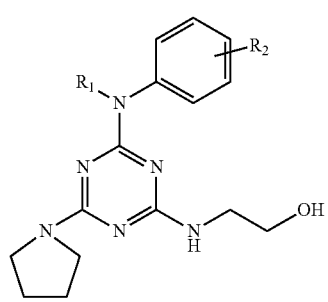
[Formula 10]
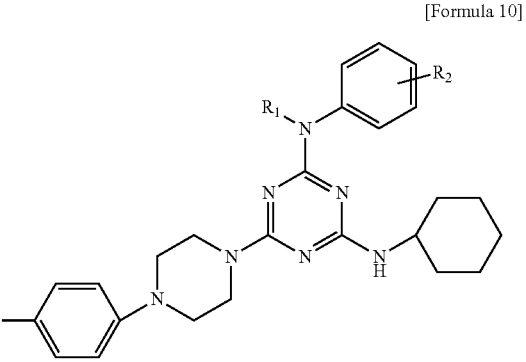

[Formula 11]

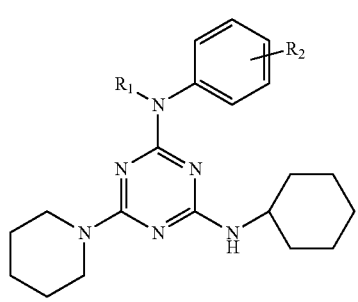

[Formula 12]

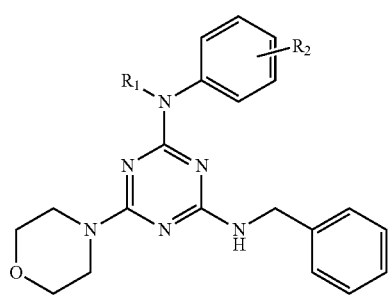

wherein,
R₁ is H; and
R₂ is —(CH₂)$_q$—(CONH)—C$_{1-5}$ straight or branched alkyl (q is an integer of 1 to 2), —(CH₂)$_q$—(CONH)—C$_{1-5}$ straight or branched alkyl alcohol (q is an integer of 1 to 2), —(CH₂)$_q$—(CONH)—[(CH₂)$_m$—O]$_n$—(CH₂)$_p$—NH₂ (each of m, n and p is an integer of 1 to 5, respectively, and q is an integer of 1 to 2), —(CH₂)$_q$—(CONH)—[(CH₂)$_m$—O]$_n$—CH₃ (each of m and n is an integer of 1 to 5, respectively, and q is an integer of 1 to 2) or —(CH₂)$_q$—(CONH)—[(CH₂)$_m$—O]$_n$—(CH₂)$_p$—CH₃ (each of m, n and p is an integer of 1 to 5, respectively, and q is an integer of 1 to 2); and the triazine-based compound does not comprise compounds represented by the following Formulae 19 and 20:

[Formula 19]

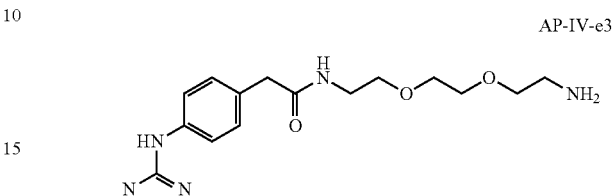

AP-IV-e3

[Formula 20]

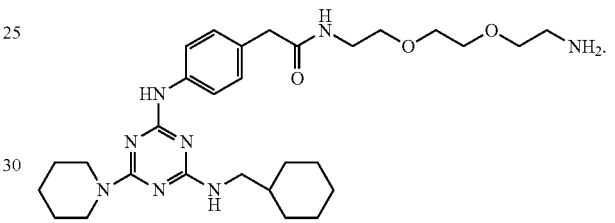

AP-IV-e4

3. The method according to claim 2, wherein the triazine-based compound comprises compounds represented by the following Formulae 13-18 and 21-30:

[Formula 13]

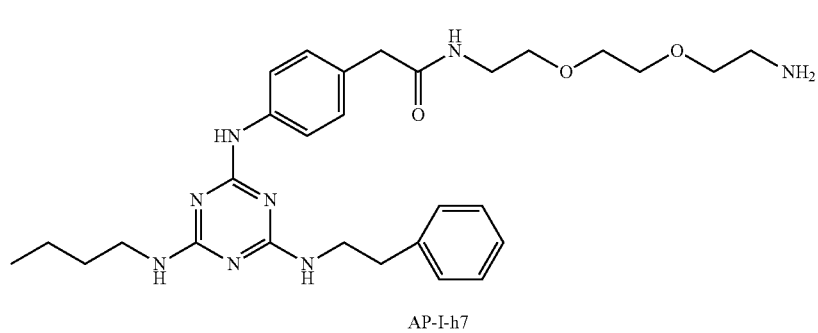

AP-I-h7

[Formula 14]

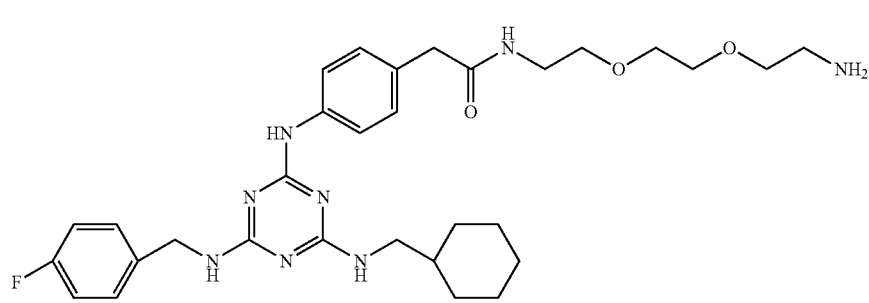

AP-III-a4

-continued
[Formula 15]
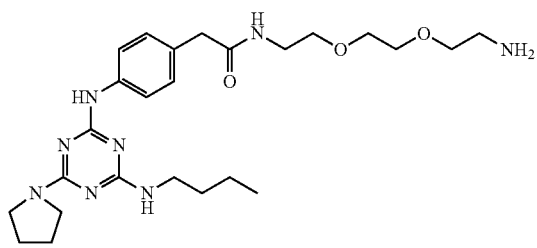
AP-IV-g3
[Formula 16]
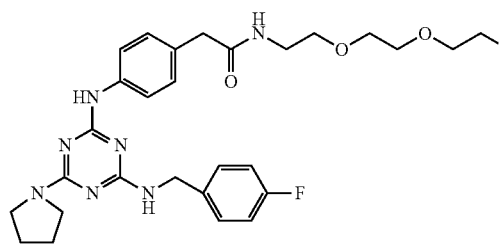
AP-IV-g8
[Formula 17]
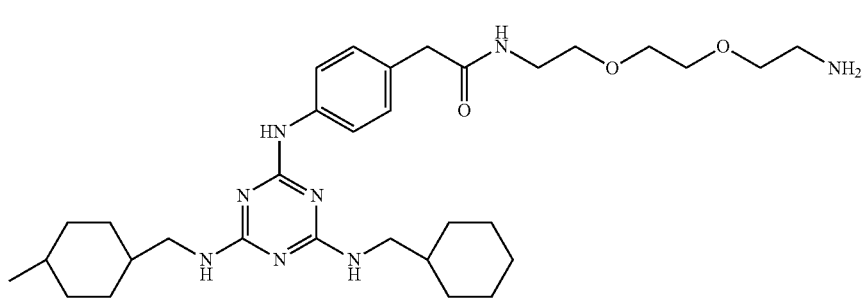
AP-IV-a4
[Formula 18]
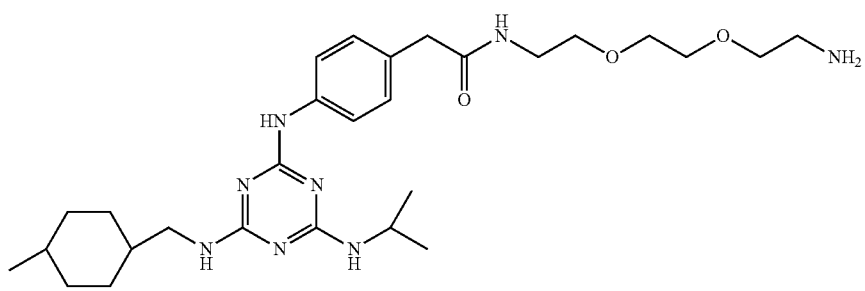
AP-IV-a10
[Formula 21]
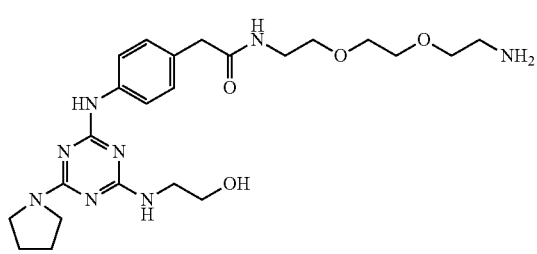
AP-IV-g12
[Formula 22]
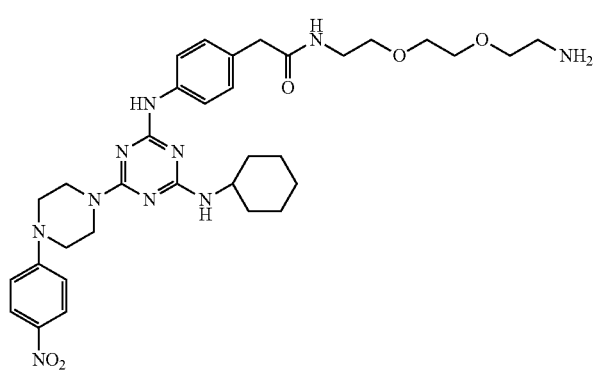
AP-IV-b5

[Formula 23]
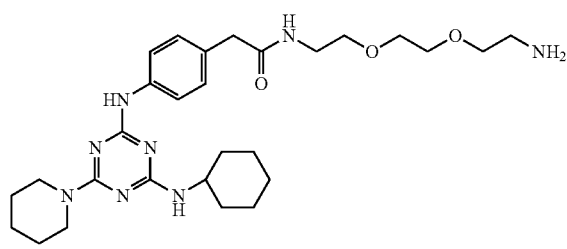
AP-IV-e5
[Formula 24]
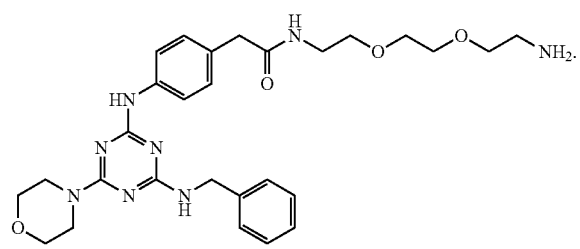
AP-IV-h2
[Formula 25]
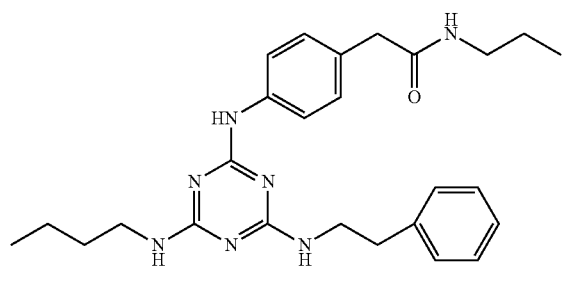
API-h7-PR
[Formula 26]
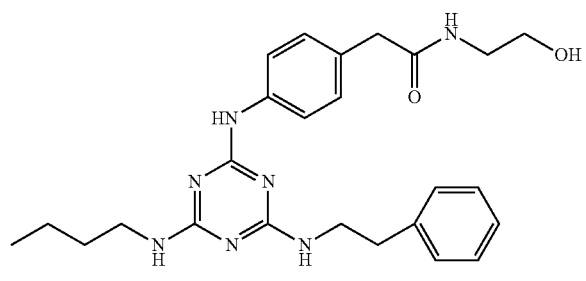
API-h7-EO
[Formula 27]
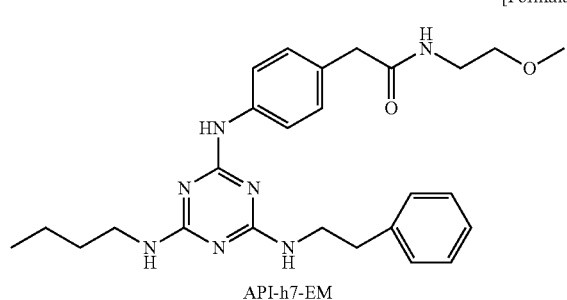
API-h7-EM
[Formula 28]
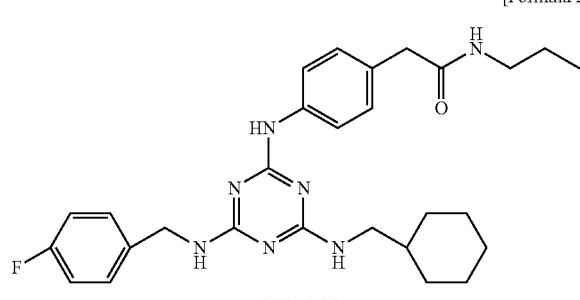
APIII-a4-PR
[Formula 29]
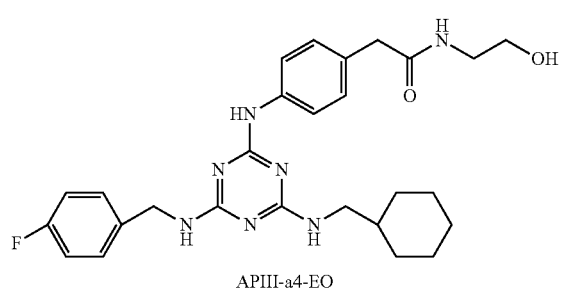
APIII-a4-EO
[Formula 30]
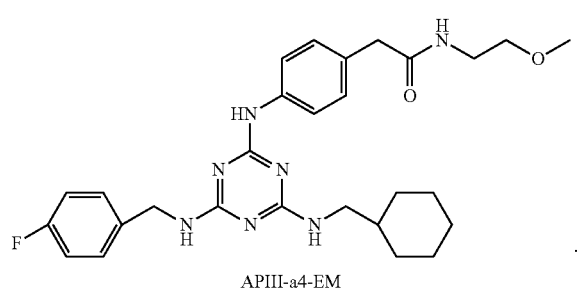
APIII-a4-EM
* * * * *